(12) United States Patent
Yano et al.

(10) Patent No.: US 9,255,041 B2
(45) Date of Patent: Feb. 9, 2016

(54) METHOD FOR PRODUCING CONJUGATED DIOLEFIN AND APPARATUS FOR PRODUCTION

(75) Inventors: Hiroyuki Yano, Tokyo (JP); Haruhiko Watanabe, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 178 days.

(21) Appl. No.: 14/118,166

(22) PCT Filed: May 9, 2012

(86) PCT No.: PCT/JP2012/061903
§ 371 (c)(1),
(2), (4) Date: Jan. 7, 2014

(87) PCT Pub. No.: WO2012/157495
PCT Pub. Date: Nov. 22, 2012

(65) Prior Publication Data
US 2014/0114108 A1 Apr. 24, 2014

(30) Foreign Application Priority Data
May 19, 2011 (JP) ................................. 2011-112284

(51) Int. Cl.
| | | |
|---|---|---|
| *C07C 7/152* | (2006.01) | |
| *B01J 23/88* | (2006.01) | |
| *C07C 2/10* | (2006.01) | |
| *C07C 5/48* | (2006.01) | |
| *C07C 7/10* | (2006.01) | |
| *B01J 21/08* | (2006.01) | |
| *B01J 23/00* | (2006.01) | |
| *B01J 23/883* | (2006.01) | |
| *B01J 37/00* | (2006.01) | |
| *B01J 37/02* | (2006.01) | |
| *C08F 36/06* | (2006.01) | |
| *C08F 136/06* | (2006.01) | |

(52) U.S. Cl.
CPC . *C07C 2/10* (2013.01); *B01J 21/08* (2013.01); *B01J 23/002* (2013.01); *B01J 23/883* (2013.01); *B01J 37/0045* (2013.01); *B01J 37/0201* (2013.01); *C07C 5/48* (2013.01); *C07C 7/10* (2013.01); *C08F 36/06* (2013.01); *C08F 136/06* (2013.01); *B01J 2523/00* (2013.01); *C07C 2521/04* (2013.01); *C07C 2521/06* (2013.01); *C07C 2521/08* (2013.01); *C07C 2523/02* (2013.01); *C07C 2523/04* (2013.01); *C07C 2523/10* (2013.01); *C07C 2523/18* (2013.01); *C07C 2523/755* (2013.01); *C07C 2523/881* (2013.01); *C07C 2523/883* (2013.01)

(58) Field of Classification Search
CPC .............. C07C 5/48; C07C 2/10; C07C 7/10; C07C 11/167; C07C 2523/883; C07C 2523/881; C07C 2523/755; C07C 2523/02; C07C 2523/04; C07C 2521/06; C07C 2521/08; B01J 37/0201; B01J 37/0045; B01J 23/883; B01J 23/002; B01J 21/08; B01J 2523/00
See application file for complete search history.

(56) References Cited

U.S. PATENT DOCUMENTS

| | | | |
|---|---|---|---|
| 3,278,625 A | 10/1966 | Dancer | |
| 3,299,163 A | 1/1967 | Zelinski | |
| 4,587,369 A | 5/1986 | Cosyns et al. | |
| 4,987,252 A | 1/1991 | Kuragano et al. | |
| 5,801,266 A * | 9/1998 | Ishii .............................. 558/320 |
| 8,546,634 B2 * | 10/2013 | Midorikawa et al. .. B01J 23/002 502/302 |

FOREIGN PATENT DOCUMENTS

| | | |
|---|---|---|
| EP | 0 094 699 A | 11/1983 |
| JP | 49-6283 A | 1/1974 |
| JP | 58-210028 A | 12/1983 |
| JP | 60-109530 A | 6/1985 |
| JP | 60-193931 A | 10/1985 |
| JP | 61-5030 A | 1/1986 |
| JP | 2010-90082 A | 4/2010 |
| TW | 200630330 A | 9/2005 |
| WO | WO 2013/136434 A1 | 9/2013 |

OTHER PUBLICATIONS

European Search Report issued Dec. 1, 2014, in European Patent Application No. 12786240.7.
English translation of International Preliminary Report on Patentability and Written Opinion mailed Nov. 28, 2013, in PCT International Application No. PCT/JP2012/061903.
English translation of International Search Report issued Aug. 14, 2012, in PCT International Application No. PCT/JP2012/061903.
Office Action issued Feb. 13, 2014, in Taiwanese Patent Application No. 101117449.

* cited by examiner

*Primary Examiner* — Nathan M Nutter
(74) *Attorney, Agent, or Firm* — Birch, Stewart, Kolasch & Birch, LLP

(57) ABSTRACT

A method for producing a conjugated diolefin that can suppress reaction byproducts with high boiling point from remaining in steps following a quenching step by a quenching tower, and producing a conjugated diolefin (e.g., 1,3-butadiene) that can be used as a raw material for synthetic rubber, resin and the like, even when using an industrial grade mixed hydrocarbon that may not necessarily have a high purity as a raw material to produce the conjugated diolefin (e.g., butadiene). The method includes a step of producing a product gas by reaction containing a conjugated diolefin by feeding a hydrocarbon containing a monoolefin having 4 or more carbon atoms and oxygen to a reactor accommodated with a catalyst containing a metal oxide and a carrier, and a step of sending the product gas by reaction to a quenching tower and washing with a quenching agent (e.g., an organic amine aqueous solution).

8 Claims, 7 Drawing Sheets

US 9,255,041 B2

METHOD FOR PRODUCING CONJUGATED DIOLEFIN AND APPARATUS FOR PRODUCTION

BACKGROUND OF THE INVENTION

1. Field of the Invention

The present invention relates to a method for producing a conjugated diolefin and an apparatus for the production.

2. Description of the Related Art

Conjugated diolefins, such as 1,3-butadiene (hereinafter, also referred to simply as "butadiene") and isoprene, are industrially produced from a naphtha pyrolysis hydrocarbon mixture based on a separation purification/recovery method by extraction or extractive distillation, and are used as raw materials for synthetic rubber, resin and the like. According to the Japanese Industrial Standards (JIS K 1533-1980), the purity of butadiene is defined as 98.0% or more. Thus, when butadiene or isoprene is used as an industrial raw material, a high purity is demanded. The reason for this is that when producing synthetic rubber, resin and the like by polymerizing butadiene or isoprene that contains impurities, the impurities could inhibit polymerization of the butadiene or isoprene or cause the polymerization to proceed excessively, causing the physical properties of the obtained synthetic rubber, resin and the like to deteriorate.

Conventionally, a separation purification method of a naphtha pyrolysis product has been employed for industrial butadiene production. Impurities that are known to be produced in this method include acetylenes and carbonyl compounds. However, these are sufficiently removed by extractive distillation using a polar solvent, such as N,N-dimethylformamide (DMF). The resultant product is used as a raw material for synthetic rubber, resin and the like by purifying until it satisfies the standard.

In addition to naphtha pyrolysis, other known methods to produce butadiene and isoprene include catalytic oxidative dehydrogenation of n-butene or isopentene. This method is known to produce, other than the target butadiene and isoprene, various reaction byproducts, such as organic acids, aldehydes, and compounds with high boiling point, that cannot be produced in a naphtha pyrolysis method, because this method employs an oxidation reaction in which oxygen is involved. Some of these byproducts are present in the product gas as fine solid particles. Patent Document 1 describes a method in which butadiene produced using, for a raw material, BBSS (a mixture mainly of hydrocarbons having 3 to 5 carbon atoms), which is obtained by separating butadiene and isoprene from a C4 fraction obtained by naphtha pyrolysis, is purified by setting the concentration of acetylene-based hydrocarbons in the product gas to a specified level or less, quenching the resultant product gas with cooling water, recovering the product in a solvent such as DMF, and then performing extractive distillation. Further, Patent Document 2 describes a method in which a product gas by reaction containing butadiene obtained by catalytic oxidative dehydrogenation of n-butene is sent to a quenching tower, and a byproduct with high boiling point mainly composed of organic acids is removed by dissolving in an aqueous phase by charging an alkali into the chilled water to be fed to the top of the quenching tower. In addition, Patent Document 2 also describes providing a scrubber at the outlet of the quenching tower to trap the solid particles produced as byproducts.

CITATION LISTS

Patent Document

Patent Document 1: Japanese Patent Laid-Open No. 2000-90082

Patent Document 2: Japanese Patent Laid-Open No. 61-5030

Technical Problem

There are various byproducts from an oxidation reaction, as is shown by the description in Patent Document 2 that even solid byproducts are produced. When using a hydrocarbon mixture like BBSS for a raw material, the variety of byproducts becomes much greater. Consequently, based on investigations by the present inventors, it was learned that in a method that quenches a product gas by reaction with cooling water as described in Patent Document 1, not only is it impossible to sufficiently remove the organic acids, aldehydes, ketones, and compounds with high boiling point produced in the side reaction, but the problem is that trouble arises in continuing operation as a result of the reaction byproducts turning into droplets due to condensation by the cooling water, accompanying the reaction gas flow and causing blockages in the pipes and equipment.

The method described in Patent Document 2 is considered to have an effect of neutralizing and dissolving the organic acids included in the product gas by washing the gas with an aqueous alkali solution. However, based on investigations by the present inventors, it is impossible to satisfactorily remove other byproducts. In addition, although the method described in Patent Document 2 is considered to have a solid particle trapping effect due to having a scrubber at the outlet of the quenching tower, over time some of the solid particles accumulate in the connecting pipes between the top of the quenching tower and the scrubber before the particles reach the scrubber, so that pipe blockages will occur.

On the other hand, the product gas by reaction containing butadiene obtained by the methods described in Patent Documents 1 and 2 could conceivably be purified by diverting the product gas by reaction to a naphtha pyrolysis purification step after undergoing the quenching step. However, based on investigations by the present inventors, it was learned that some of the reaction byproducts, specifically 4-methyl-4-formyl-1-cyclohexene and methacrolein, contaminate the product butadiene as impurities without being sufficiently reduced. Further, in the reaction for producing butadiene with n-butene as a raw material, since isobutene is not present, 4-methyl-4-formyl-1-cyclohexene and methacrolein are not produced as byproducts. When producing synthetic rubber, resin and the like using product butadiene contaminated with such impurities for a raw material, for example, the polymerization rate deteriorates, the degree of polymerization decreases, and the molecular weight distribution expands. Consequently, it was also learned that a problem is that even the mechanical physical properties, processability and the like of the obtained synthetic rubber, resin and the like are harmed.

Accordingly, it is an object of the present invention to provide a method for producing a conjugated diolefin that includes a step of sending a product gas by reaction produced by catalytic oxidative dehydrogenation of a hydrocarbon containing a monoolefin having 4 or more carbon atoms, in which reaction byproducts, especially compounds with high boiling point, remaining in steps following a quenching step by a quenching tower can be suppressed. Further, it is also an object of the present invention to provide a method for producing a conjugated diolefin (e.g., butadiene) that can be used as a raw material for synthetic rubber, resin and the like, even when using a so-called industrial grade mixed hydrocarbon, such as BBSS, that may not necessarily have a high purity as a raw material to produce the conjugated diolefin (e.g., butadiene).

SUMMARY OF THE INVENTION

As a result of diligent research to achieve the above-described objects, the present inventors discovered that impurities such as 4-methyl-4-formyl-1-cyclohexene and methacrolein can be efficiently removed from a product gas by reaction containing a conjugated diolefin produced by catalytic oxidative dehydrogenation by sending the product gas by reaction to a quenching tower, and then washing the product gas by reaction with a specific quenching agent, thereby completing the present invention. The conjugated diolefin and polymerization product thereof obtained by the production method according to the present invention can be used as a raw material for synthetic rubber, resin and the like, in the same manner as a conjugated diolefin obtained by known naphtha pyrolysis product separation purification.

Specifically, the present invention is as follows.

[1] A method for producing a conjugated diolefin, comprising:

a step of feeding a hydrocarbon containing a monoolefin having 4 or more carbon atoms and oxygen to a reactor accommodated with a catalyst which comprises a metal oxide and a carrier to produce a product gas by reaction containing a conjugated diolefin by feeding a hydrocarbon containing a monoolefin having 4 or more carbon atoms and oxygen to a reactor accommodated with a catalyst which comprises a metal oxide and a carrier; and a step of sending the product gas by reaction to a quenching tower and washing with a quenching agent, wherein an organic amine aqueous solution is used as the quenching agent.

[2] The method for producing the conjugated diolefin according to [1], wherein an aromatic organic solvent is used in combination as the quenching agent.

[3] The method for producing the conjugated diolefin according to [1] or [2], wherein a withdrawn liquid from the quenching tower contains at least one compound selected from the group consisting of 4-methyl-4-formyl-1-cyclohexene, methacrolein, methacrylic acid, benzoic acid, acetic acid, acrylic acid, and an organic amine salt of these.

[4] The method for producing the conjugated diolefin according to any of [1] to [3], wherein the quenching tower has a plurality of vertical sections, an aromatic organic solvent is used as the quenching agent at a lowest section among the plurality of sections, and an organic amine aqueous solution is used as the quenching agent at a section above the lowest section.

[5] The method for producing the conjugated diolefin according to any of [1] to [4], wherein the organic amine contains at least one compound selected from the group consisting of monoethanolamine, diethanolamine, and triethanolamine.

[6] The method for producing the conjugated diolefin according to [2], wherein the aromatic organic solvent contains at least one compound selected from the group consisting of o-xylene, m-xylene, p-xylene, and a mixed xylene.

[7] The method for producing the conjugated diolefin according to any of [1] to [6], wherein the metal oxide is represented by the following experimental formula (1):

$$Mo_{12}Bi_pFe_qA_aB_bC_cD_dE_eO_x \quad (1)$$

wherein A represents at least one element selected from the group consisting of nickel and cobalt; B represents at least one element selected from the group consisting of alkali metal elements; C represents at least one element selected from the group consisting of magnesium, calcium, strontium, barium, zinc, and manganese; D represents at least one element selected from the group consisting of rare earth elements; E represents at least one element selected from the group consisting of chromium, indium, and gallium; O represents oxygen; p, q, a, b, c, d, e, and x denote an atomic ratio of bismuth, iron, A, B, C, D, E, and O respectively, to 12 molybdenum atoms, where $0.1 \leq p \leq 5$, $0.5 \leq q \leq 8$, $0 \leq a \leq 10$, $0.02 \leq b \leq 2$, $0 \leq c \leq 5$, $0 \leq d \leq 5$, and $0 \leq e \leq 5$; and x denotes the number of oxygen atoms required to satisfy the valence requirements of the other elements that are present.

[8] The method for producing the conjugated diolefin according to any of [1] to [7], wherein the reactor is a fluidized bed reactor.

[9] An apparatus for a conjugated diolefin production, comprising:

a reactor accommodated with a catalyst which comprises a metal oxide and a carrier; and a quenching tower connected to the reactor, wherein a product gas by reaction containing a conjugated diolefin produced by feeding a hydrocarbon containing a monoolefin having 4 or more carbon atoms and oxygen to the reactor flows into the quenching tower, the product gas by reaction is washed with a quenching agent in the quenching tower, and an organic amine aqueous solution is used as the quenching agent.

[10] The apparatus for the conjugated diolefin production according to [9], wherein an aromatic organic solvent is used in combination as the quenching agent.

Advantageous Effects of Invention

According to the present invention, a conjugated diolefin (e.g., butadiene) can be produced that can be used as a raw material for synthetic rubber, resin and the like, without causing blockages in pipes or equipment, by catalytic oxidative dehydrogenation of a hydrocarbon containing a monoolefin having 4 or more carbon atoms.

DETAILED DESCRIPTION OF THE PREFERRED EMBODIMENTS

Figure 1:
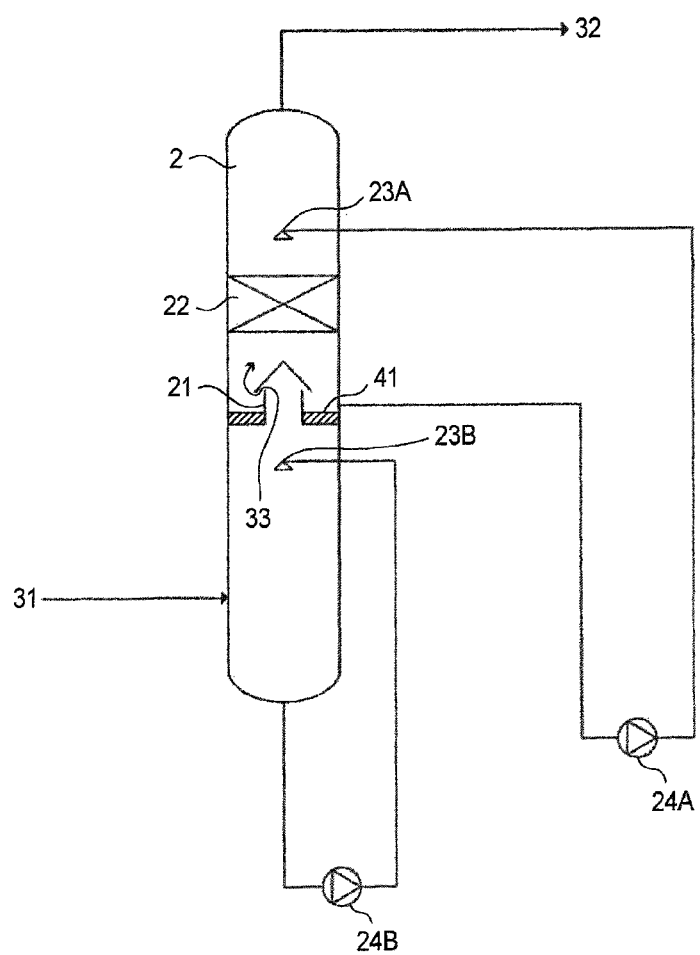
FIG. 1 is a diagram schematically illustrating an example of a quenching tower used in a method for producing a conjugated diolefin according to the present embodiment.

An embodiment for carrying out the present invention (hereinafter, "present embodiment") will now be described in more detail. However, the present invention is not limited to the following embodiment, and can be carried out with various modifications made within the scope thereof.

[1] Conjugated Diolefin Production Method

The method for producing the conjugated diolefin according to the present embodiment includes:

a step of feeding a hydrocarbon containing a monoolefin having 4 or more carbon atoms and oxygen (hereinafter, a raw material gas containing this hydrocarbon and oxygen is also referred to as "raw material mixed gas") to a reactor accommodated with a catalyst which comprises a metal oxide and a carrier to produce a product gas by reaction containing a conjugated diolefin; and a step of sending the product gas by reaction to a quenching tower and washing with a quenching agent, wherein an organic amine aqueous solution is used as the quenching agent.

In the production method according to the present embodiment, the conjugated diolefin is produced by catalytic oxidative dehydrogenation of a hydrocarbon containing a monoolefin having 4 or more carbon atoms. Examples of the target conjugated diolefin include 1,3-butadiene, isoprene and the like, and 1,3-butadiene is preferred.

(1) Hydrocarbon Raw Material

The hydrocarbon raw material contains a monoolefin having 4 or more carbon atoms. Since monoolefins have only one carbon-carbon double bond, generally monoolefins are an organic compound that does not have a functional group, and are a straight chain and/or branched chain hydrocarbons. Although the upper limit of the number of carbon atoms in the monoolefin is not strictly limited, from the perspective of reactivity, an upper limit of 6 or less is preferred. Examples of the monoolefin having 4 or more carbon atoms include n-butene (1-butene, 2-butene), isobutene, 1-pentene, 2-pentene, isopentene (2-methyl-1-butene, 3-methyl-1-butene), 1-hexene, 2-hexene, 2,3-dimethyl-butene and the like. One type of the monoolefin may be used as the raw material, or two or more types can be used. It is preferred to use in the reaction a monoolefin that is a liquid at ordinary temperatures (5 to 35° C.) after gasification using steam or a gasification apparatus having a heating unit such as a heat-conductive coil.

The hydrocarbon raw material does not necessarily have a high purity. An arbitrary mixture or an industrial grade product can be used for the hydrocarbon raw material. Examples of hydrocarbon raw materials that can be used include a residual fraction (BBS) obtained by extracting butadiene from a C4 fraction produced as a byproduct from naphtha pyrolysis or the residual fraction (BBSS) obtained by further separating isobutene, the C4 fraction produced as a byproduct from fluid catalytic cracking (FCC) of petroleum fractions or the residual fraction obtained by further separating isobutene, the C4 fraction obtained by dehydrogenation or oxidative dehydrogenation of n-butene, and the C4 fraction obtained by catalytic conversion of n-butene obtained by dimerization of ethylene, ethylene, or ethanol, or the residual fraction obtained by further separating isobutene. The isobutene can be separated by skeletal isomerization, selective adsorption, dimerization and the like of methyl-tert-butyl ether (MTBE), ethyl-tert-butyl ether (ETBE), or n-butene by reacting with t-butyl alcohol (TBA) or an alcohol based on a hydration reaction. As the ethylene, ethylene obtained by naphtha pyrolysis, ethane pyrolysis, or dehydration of ethanol can be used. As the ethanol, industrial ethanol and biomass ethanol can be used. Biomass ethanol is obtained from a plant resource. Specifically, examples include ethanol obtained from fermentation of sugar cane, corn and the like, and ethanol obtained from ligneous resources such as scrap wood, thinnings, rice straw, agricultural crops and the like.

From the perspective of conjugated diolefin productivity, the concentration of the monoolefin in the raw material is, for example, based on 100% by volume of the raw material mixed gas containing at least the monoolefin and air, preferably 2% by volume or more, and from the perspective of suppressing the load on the catalyst, preferably 30% by volume or less. More preferably, the monoolefin concentration is 3 to 25% by volume. If the monoolefin concentration in the raw material is high, accumulation of the reaction product tends to increase, coke deposition tends to increase, and the catalyst life tends to decrease due to catalyst deactivation.

The raw material mixed gas may also include paraffin, water, steam, hydrogen, nitrogen, carbon dioxide, carbon monoxide and the like. Examples of paraffin include methane, ethane, propane, butane, pentane, hexane, heptane, octane, and nonane. Further, after the butadiene, which is the target product, has been separated from the reaction product, at least a part of the unreacted butene may be recycled back to the fluidized bed reactor.

(2) Reactor

The conjugated diolefin production by catalytic oxidative dehydrogenation of the hydrocarbon containing the monoolefin having 4 or more carbon atoms can be carried out by employing a fluidized bed reactor, a fixed bed reactor, or a moving bed reactor. Preferably, the reactor is a fluidized bed reactor.

The fluidized bed reactor has a reactor, a gas disperser provided in the reactor, an insertion material for maintaining the fluidized state in a good condition, and a cyclone as main constituent elements, and is configured so that a catalyst pre-accommodated in the reactor comes into contact with a raw material gas while being made to flow by an air current. Although any fluidized bed reactor described in the Fluidized Bed Handbook (published by Baifukan Co., Ltd., 1999), for example, can be used, a bubbling fluidized bed type reactor is especially suitable. The heat generated in the reaction can be removed using a cooling pipe inserted into the reactor.

(3) Reaction Conditions

A hydrocarbon containing a monoolefin having 4 or more carbon atoms and oxygen are used in the reaction. Although air is usually used as an oxygen source, a gas having an increased oxygen concentration produced, for example, by mixing oxygen and air, or a gas having a decreased oxygen concentration produced, for example, by mixing air with an inert gas such as helium or nitrogen, can also be used. The molar ratio of the monoolefin relative to oxygen is preferably, in terms of monoolefin/oxygen, 0.4 to 2.5, and more preferably 0.6 to 2.1. If the molar ratio of the monoolefin relative to oxygen is 2.5 or less, degradation of the produced conjugated diolefin tends to be suppressed, and if this molar ratio is 0.4 or more, the reactivity of the monoolefin tends to be improved.

The method for introducing the hydrocarbon containing a monoolefin having 4 or more carbon atoms and the oxygen into the reactor is not limited. A gas containing the hydrocarbon containing a monoolefin having 4 or more carbon atoms can be pre-mixed with air or a gas having an increased oxygen concentration, and the resultant mixture can be introduced into the reactor accommodated with a catalyst, or the respective gases can be introduced individually. Further, a method that introduces the gases used in the reaction in the above-described ratio is preferred. In addition, although the temperature of the gases used in the reaction can be increased to a predetermined reaction temperature after introduction into the reactor, to efficiently perform the reaction continuously, these gases are usually preheated and then introduced into the reactor.

The reaction temperature is preferably set to 300 to 420° C. If the reaction temperature is 300° C. or more, monoolefin conversion tends to occur easily, while a reaction temperature of 420° C. or less tends to enable combustion decomposition of the produced conjugated diolefin to be kept at a low level. A more preferred reaction temperature is 300 to 400° C., and especially preferable is 310 to 390° C. Since the conjugated diolefin production reaction is an exothermic reaction, usually, heat is removed so that the temperature is at the preferred reaction temperature. The reaction temperature can also be regulated to within the above-described range by removing the reaction heat with a cooling pipe or supplying heat with a heating apparatus.

The reaction pressure can be set to a slightly pressurized condition to 0.8 MPa. A contact time between the raw material mixed gas and the catalyst is 0.5 to 20 (sec·g/cc), and preferably 1 to 10 (sec·g/cc). The contact time is defined based on the following equation.

$$\text{Contact Time (g·sec/cc)} = \frac{w \times 3.6 \times 273.15 \times (P \times 1000 + 101.325)}{F \times (273.15 + T) \times 101.325} \quad \text{[Equation 1]}$$

wherein W represents the catalyst amount (g), F represents the raw material mixed gas flow rate (NL/hr, based on NTP (value based on 0° C., 1 atm)), T represents the reaction temperature (° C.), and P represents the reaction pressure (MPaG).

By bringing the catalyst and the raw material mixed gas into contact with each other in the reactor, a conjugated diolefin corresponding to the monoolefin is produced. Since the selectivity and/or yield of the product depend on the raw materials, catalyst, reaction temperature and the like, these conditions may be appropriately set so that the yield and/or selectivity are preferred values. For example, if the monoolefin is n-butene, the main product is butadiene, while if the monoolefin is isopentene, the main product is isoprene. When isobutene contacts with the catalyst for conjugated diolefin production, for example, methacrolein, methacrylic acid, and 4-methyl-4-formyl-1-cyclohexene, which is an adduct of methacrolein and butadiene, are produced from the isobutene. When using BBSS, which is produced by separating isobutene from BBS, as the hydrocarbon raw material, a small amount of isobutene usually remains even after the separation step. Therefore, 4-methyl-4-formyl-1-cyclohexene and methacrolein are also produced when BBSS is used for the hydrocarbon raw material. Further, since 4-methyl-4-formyl-1-cyclohexene is produced by an addition reaction of butadiene and methacrolein, production of 4-methyl-4-formyl-1-cyclohexene means that the recovery ratio of butadiene decreases.

(4) Quenching Step

The method for producing the conjugated diolefin according to the present embodiment includes a step of sending the product gas by reaction to a quenching tower and washing with a quenching agent (hereinafter, also referred to as "quenching step").

In the quenching step, it is preferred to use an organic amine aqueous solution as the quenching agent, and to also use an aromatic organic solvent in combination. By using an aromatic organic solvent in combination with the organic amine aqueous solution as the quenching agent, a higher purity conjugated diolefin can be obtained.

In the quenching step, for example, the product gas by reaction is sent from the bottom of the quenching tower to a quenching section, and rises up inside the quenching tower. Since an organic amine aqueous solution and an aromatic organic solvent (hereinafter also referred to as "aromatic solvent"), for example, are sprayed in the quenching tower, the product gas by reaction is washed by coming into contact with the organic amine aqueous solution and the aromatic solvent, and then ran out from the top of the tower. Due to this washing, for example, reaction byproducts in the product gas by reaction, such as organic acids, aldehydes, and compounds with high boiling point, are removed by dissolving in the organic amine aqueous solution and the aromatic solvent and reacting with the organic amine. For example, among the reaction byproducts, the low boiling point organic acids, aldehydes, and ketones, such as acetic acid, methacrylic acid, maleic acid, crotonaldehyde, and methyl vinyl ketone, are removed from the product gas by reaction mainly by dissolving in and reacting with the organic amine aqueous solution, and compounds with high boiling point, such as benzoic acid, are removed from the product gas by reaction mainly by dissolving in the aromatic solvent.

In the conjugated diolefin production by catalytic oxidative dehydrogenation, in addition to the main reaction of producing a diolefin from an olefin, for example, because the reaction is oxidative, a side reaction proceeds in which oxygen-containing compounds such as organic acids, aldehydes, and ketones are produced, and a secondary reaction proceeds in which the produced diolefin and side reaction products serve as reaction raw materials. Especially when using BBSS for a raw material, the main reaction, side reaction, and secondary reaction proceed in a more complex manner than when using only n-butene that has 4 carbon atoms for a raw material. This is due to the fact that since BESS is a mixture mainly of hydrocarbons having 3 to 5 carbon atoms, a large amount of hydrocarbons that can serve as reaction raw materials is present, so that compared with when using only n-butene that has 4 carbon atoms for the raw material, a very large variety of reaction byproducts is produced, including side reaction products such as oxygen-containing compounds and secondary reaction products between the target butadiene and the side reaction products. Generally, catalytic oxidative dehydrogenation involving multiple kinds of hydrocarbons easily produces compounds with high boiling point from side reactions, and the water solubility of the reaction byproducts tends to be low.

Examples of the components that are produced when a hydrocarbon raw material from which isobutene has not been completely removed, such as BBSS, is used for the raw material of the conjugated diolefin include 4-methyl-4-formyl-1-cyclohexene, methacrolein, methacrylic acid and the like. Among these, when quenching the product gas by reaction using a quenching agent (e.g., sodium hydroxide aqueous solution) other than an organic amine aqueous solution, like in naphtha pyrolysis, the 4-methyl-4-formyl-1-cyclohexene and methacrolein contaminate the product butadiene as impurities without being sufficiently separated. The present inventors thought that this contamination of 4-methyl-4-formyl-1-cyclohexene and methacrolein is due to the compatibility between these reaction byproducts and the butadiene and conventionally used purification solvent. Further, since the present inventors discovered that 4-methyl-4-formyl-1-cyclohexene and methacrolein act as butadiene polymerization inhibitors, the present inventors thought that the purification solvent for purifying butadiene should be selected by focusing on especially the affinity with these reaction byproducts. To resolve such a problem, the present inventors discovered that when using a hydrocarbon raw material from which isobutene has not been completely removed, such as BBSS, for the raw material of the conjugated diolefin, the use of an organic amine aqueous solution as the quenching agent of the product gas by reaction has a good effect in removing 4-methyl-4-formyl-1-cyclohexene and/or methacrolein.

On the other hand, benzoic acid, phthalic acid, phenol, benzophenone, 9-fluorenone and the like are not a mixture like BBSS, but are reaction byproducts with high boiling point produced even when a monoolefin like n-butene is used alone for the hydrocarbon raw material. These reaction byproducts are detected in microscopic solid particles adhered to the piping equipment in the steps following the quenching step in the quenching tower by repeatedly performing a purification test on the butadiene. Based on this fact, the present inventors discovered that these reaction byproducts have in common the physical property that they are sublimable. Accordingly, to remove these reaction byproducts, from the perspective of removing by dissolution in addition to quenching with an organic amine aqueous solution, the present inventors thought that a quenching agent having even better compatibility in dissolution with the byproducts should be selected. Specifically, the present inventors discovered that when producing a conjugated diolefin using as a raw material a hydrocarbon raw material that includes n-butene, such as n-butene and BBSS, by using an aromatic organic solvent in addition to an organic amine aqueous solution for the product gas by reaction quenching agent, an effect of removing reaction byproducts with high boiling point that are sublimable, such as benzoic acid, phthalic acid, phenol, benzophenone, and 9-fluorenone, can be obtained. The kind and amount of the byproducts depend not only on the raw materials, but also on the catalyst and reaction conditions such as the temperature and pressure, and the optimum quenching agent will vary based on the composition of the byproducts. Therefore, the knowledge of selecting the quenching agent from the perspective of compatibility in dissolution with the components to be removed is very useful in industrially carrying out conjugated diolefin production.

In the method for producing the conjugated diolefin according to the present embodiment, it is preferred that the withdrawn liquid from the quenching tower contains at least one compound selected from the group consisting of 4-methyl-4-formyl-1-cyclohexene, methacrolein, methacrylic acid, benzoic acid, acetic acid, acrylic acid, and an organic amine salt of these. If the withdrawn liquid from the quenching tower includes such a compound, the obtained conjugated diolefin has a higher purity. Further, in the present embodiment, the withdrawn liquid from the quenching tower includes not only the liquid that is withdrawn from the bottom of the tower (tower bottom liquid), but if the interior of the quenching tower is formed from a plurality of sections, also the liquid withdrawn from each section.

From the perspective of efficiently bringing the quenching agent into contact with the product gas by reaction, it is preferred that the quenching tower is a multistage quenching tower having two or more sections in its interior, and more preferably having three or more sections. In the quenching tower, the quenching agent withdrawn at each section is sprayed as a circulating liquid onto a portion above the withdrawn position to cool the product gas by reaction and remove the reaction byproducts, and then the resultant liquid is withdrawn as the withdrawn liquid from those respective sections. On the other hand, the product gas by reaction containing the conjugated diolefin (e.g., butadiene) running out from the top of the quenching tower is sent to the following step. It is preferred that organic amine aqueous solution in the withdrawn quenching agent is returned to the quenching tower after being cooled, and then re-sprayed. It is also preferred to adjust the temperature of the aromatic solvent in the withdrawn quenching agent to room temperature to 70° C. based on the boiling point, solubility, and sublimation property of the aromatic reaction byproducts. Similar to the organic amine aqueous solution, it is preferred to return the aromatic solvent to the quenching tower, and then re-spray it. Further, to reduce the burden of the inert gas degassing operation in the below-described purification step, it is preferred to control the outlet gas temperature of the quenching tower to a suitable temperature. For this control, it is effective to cool the organic amine aqueous solution in the quenching agent to a suitable temperature before re-spraying it, and then feed the cooled solution to an upper stage of the quenching tower. At this point, the temperature of the organic amine aqueous solution is controlled to 80° C. or less, and preferably in the range of 0 to 70° C., and the quenching tower outlet gas temperature is controlled to 70° C. or less, and preferably in the range of 5 to 60° C. The quenching tower can be independently provided with, for example, a first quenching tower for washing the product gas by reaction with the organic amine aqueous solution, and a second quenching tower for washing the product gas by reaction with the aromatic solvent. Each quenching tower may also be a multistage quenching tower having two or more sections in its interior.

An amount of the quenching agent to be fed can be appropriately set based on, for example, the type and temperature of the quenching agent, the type and amount of the byproducts to be removed, and the size and number of stages of the quenching tower. In a mode in which the withdrawn quenching agent is reused, the necessary amount to be fed can be provided by adding a new quenching agent in an amount corresponding to an insufficient amount provided by the quenching agent to be reused.

When using a different quenching agent in the respective stages in a multistage quenching tower, since the withdrawn liquid may be a mixture of an aqueous phase and an oil phase depending on the combination of quenching agents, it is preferred to separate the aqueous phase and the oil phase in the withdrawn liquid with a decanter prior to feeding the withdrawn liquid back to the quenching tower. For example, when using an organic amine aqueous solution and an aromatic organic solvent in combination as the quenching agent, a preferred mode is to feed the withdrawn liquid to a decanter, separate the aqueous phase and the oil phase, and then re-spray the organic amine aqueous solution and the aromatic organic solvent onto each stage.

A spray nozzle can be used to spray the quenching agent. The amount to be sprayed and the number and arrangement of spray nozzles can be appropriately determined in consideration of the contact between the quenching agent and the product gas by reaction, and the amount of product gas by reaction to be sent. Providing a void tower, tray, and filler in each section of the quenching tower is also a preferred mode. It is preferred that the pre-washing organic amine aqueous solution that is fed to the quenching tower is controlled so that it has a pH at ambient temperature of 7 to 14 during circulation, and preferably 8 to 10. The organic amine aqueous solution may be fed to the quenching tower as a solution that has already been adjusted to a predetermined concentration, or fed by mixing the organic amine and water before feeding to the quenching tower. As the quenching agent used for circulation in the quenching tower and for washing of the product gas by reaction, in addition to an organic amine aqueous solution and an aromatic solvent, water can also be used in each individual section independently in the quenching tower. The waste organic amine aqueous solution and waste aromatic solvent including the reaction byproducts discharged as a liquid from the quenching tower sections can be incinerated. Since the waste organic amine aqueous solution does not contain alkali metals that corrode the flame resistant bricks used in an incinerator, there is no risk of damage to the flame resistant bricks. Further, there is also the advantage of a decrease in an amount of NOx to be discharged in the combustion exhaust gas due to an amine non-catalytic denitrification effect, a so-called deNOx effect, so that waste liquid treatment is extremely easy. The waste aromatic solvent can be preferably utilized as a fuel.

Examples of the organic amine include amines such as monoethanolamine, diethanolamine, triethanolamine, methylamine, ethylamine, propylamine, isopropylamine, butylamine, sec-butylamine, tert-butylamine, dimethylamine, diethylamine, dipropylamine, trimethylamine, N,N-dimethylethanolamine, N,N-diethylethanolamine, N,N-dibutylethanolamine, N-methylethanolamine, N-methyldiethanolamine, N-ethylethanolamine, N-ethyldiethanolamine, N-n-butylethanolamine, N-n-butyldiethanolamine, N-tert-butylethanolamine, and N-tert-butyldiethanolamine. Preferred organic amines are monoethanolamine, diethanolamine, and triethanolamine, and an especially preferred organic amine is monoethanolamine. The monoethanolamine, which can also be used as a carbon dioxide absorbing agent, is a preferred organic amine also from the perspective of removing the carbon dioxide that is contained in the product gas by reaction. Since these amines are bifunctional compounds having an amino group and a hydroxyl group in the molecule, it is assumed that the amines remove the reaction byproducts much more effectively than a simple neutralization reaction using an aqueous alkali solution such as sodium hydroxide aqueous solution because the amines act on the organic acids contained as reaction byproducts as an amine to undergo an acid-base reaction, and act on the aldehydes as an alkali catalyst to induce aldol condensation or as an alcohol to undergo an acetal reaction.

When using an organic amine aqueous solution as the quenching agent, from the perspective of efficient removal of 4-methyl-4-formyl-1-cyclohexene, methacrolein, methacrylic acid, benzoic acid, acetic acid, acrylic acid and the like, it is preferred that the organic amine concentration in the organic amine aqueous solution is 10% by weight or more. Although a preferred upper limit for this organic amine concentration does not need to be set from a technology perspective, from an economic perspective, 80% by weight or less is preferred.

When using a conjugated diolefin as a raw material for a resin and the like, if 4-methyl-4-formyl-1-cyclohexene and/or methacrolein is included, this tends to become a cause for a deterioration in the polymerization ratio, decrease in the degree of polymerization, and an expansion in the molecular weight distribution. Consequently, it is preferred that the concentration of 4-methyl-4-formyl-1-cyclohexene and methacrolein is used as an index of the washing effect in the quenching tower. Since the amount of these compounds to be produced depends on the concentration and composition of the monoolefin in the hydrocarbon raw material, and on the reaction conditions, and also since the amount of these compounds to be dissolved in the organic amine aqueous solution depends on the quenching tower operation conditions, it is difficult to specify the concentration of 4-methyl-4-formyl-1-cyclohexene and methacrolein in the withdrawn liquid from the respective sections in the quenching tower. However, based on investigations by the present inventors, if the total of the 4-methyl-4-formyl-1-cyclohexene concentration and the methacrolein concentration in the organic amine aqueous solution withdrawn from each section is 500 ppm by weight or more, it can be determined that these compounds have been sufficiently removed from the product gas by reaction. This index was empirically derived based on the concentrations of 4-methyl-4-formyl-1-cyclohexene and methacrolein in the withdrawn liquid from the respective sections and analysis of the obtained diolefin polymerization product.

Examples of the aromatic solvent include o-xylene, m-xylene, p-xylene, a mixed xylene, toluene, ethylbenzene, diethylbenzene, 1,2,3,4,5,6,7,8-decahydronaphthalene, cumene, branched and straight-chain alkyl benzenes, pseudocumene and the like. Preferred aromatic solvents are o-xylene, m-xylene, p-xylene, and a mixed xylene, and especially preferred aromatic solvents are o-xylene and m-xylene. One type of these aromatic solvents may be used alone, or two or more types may be used in combination. Perhaps because benzoic acid that is an organic acid has a low water solubility, benzoic acid easily runs out from the quenching tower along with the product gas by reaction, and even if quenched using the organic amine aqueous solution, easily adheres to the piping equipment in the subsequent steps. However, the present inventors experimentally confirmed that by also performing washing with an aromatic solvent, benzoic acid is no longer detected. The reason for this is thought to be because benzoic acid, which is an aromatic compound just like the aromatic solvent, is effectively dissolved and removed from the product gas by reaction due to having a high compatibility in dissolution with the aromatic solvent as a result of a strong $\pi$-$\pi$ electron interaction between aromatic rings. It is thought that there is a similar removal mechanism to benzoic acid for aromatic compounds such as phthalic acid, phenol, benzophenone, and 9-fluorenone as these compounds are removed from the product gas by reaction by washing with an aromatic solvent.

Since the amount of aromatic reaction byproducts, such as benzoic acid, phthalic acid, phenol, benzophenone, and 9-fluorenone to be produced varies depending on the concentration and composition of the monoolefins in the hydrocarbon raw material and the reaction conditions, and since the amount to be dissolved in the aromatic solvent also varies depending on the quenching tower operation conditions, it is difficult to specify the concentration of the benzoic acid, phthalic acid, phenol, benzophenone, 9-fluorenone and the like in the withdrawn liquid from the respective sections in the quenching tower. However, based on investigations by the present inventors, if the concentration of benzoic acid, which is the main component among the aromatic reaction byproducts running out from the quenching tower, in the aromatic solvent withdrawn from each section is 500 ppm by weight or more, it can be determined that the aromatic reaction byproducts, such as benzoic acid, phthalic acid, phenol, benzophenone, and 9-fluorenone, have been sufficiently removed from the product gas by reaction.

Generally, the quenching tower is connected to the reactor without pressure adjustment, so that its pressure is almost the same as the reactor pressure. Therefore, to optimize the reactor pressure, the quenching tower pressure is preferably 0.01 to 0.4 MPaG, more preferably 0.02 to 0.3 MPaG, and even more preferably 0.03 to 0.2 MPaG.

In the method for producing the conjugated diolefin according to the present embodiment, it is preferred that the quenching tower has a plurality of vertical sections. A case in which the quenching tower has a plurality of vertical sections will now be described in more detail with reference to the drawings.

FIG. 1 illustrates an example of a quenching tower 2 used in the method for producing the conjugated diolefin according to the present embodiment. This quenching tower 2 is an example that has two sections, in which a chimney 21 is fitted in the middle stage and the two sections are formed above and below the chimney 21. A packed bed 22 is provided above the chimney 21. An organic amine aqueous solution is sprayed as the quenching agent from a spray apparatus 23B arranged below the chimney 21 and a spray apparatus 23A arranged above the packed bed 22.

The chimney 21 is open at a middle portion. A weir protruding upward is provided in this open portion. As illustrated in FIG. 1, the sprayed quenching agent accumulates on a tray arranged integrally on the chimney 21 (hereinafter, illustration of the quenching agent accumulated in the quenching tower will be omitted), and runs out to a circulation path. The sprayed quenching agent also accumulates at the bottom of the tower, and runs out to the circulation path. Each of the quenching agents is fed to the spray apparatuses 23A and 23B via pumps 24A and 24B for recycling. A filler is packed in the packed bed 22. At the packed bed 22, the quenching agent and the gas are efficiently brought into contact with each other while hindering the agent and the gas from going past each other. The type of filler is not especially limited. Examples that can be used include known fillers, such as Raschig rings, cascade rings, and Paul rings. The packing method is also not especially limited, and may be carried out in a regular or an irregular manner.

The product gas by reaction running out from the reactor is introduced into the quenching tower 2 from the bottom portion of the tower, and rises up inside the tower while coming into contact with the quenching agent. Further, as illustrated in FIG. 1, a part of the gas escapes through a gap in the chimney 21, passes through the packed bed 22, and runs out from the top of the tower (hereinafter, illustration of the flow of the gas in the quenching tower will be omitted).

Figure 2:
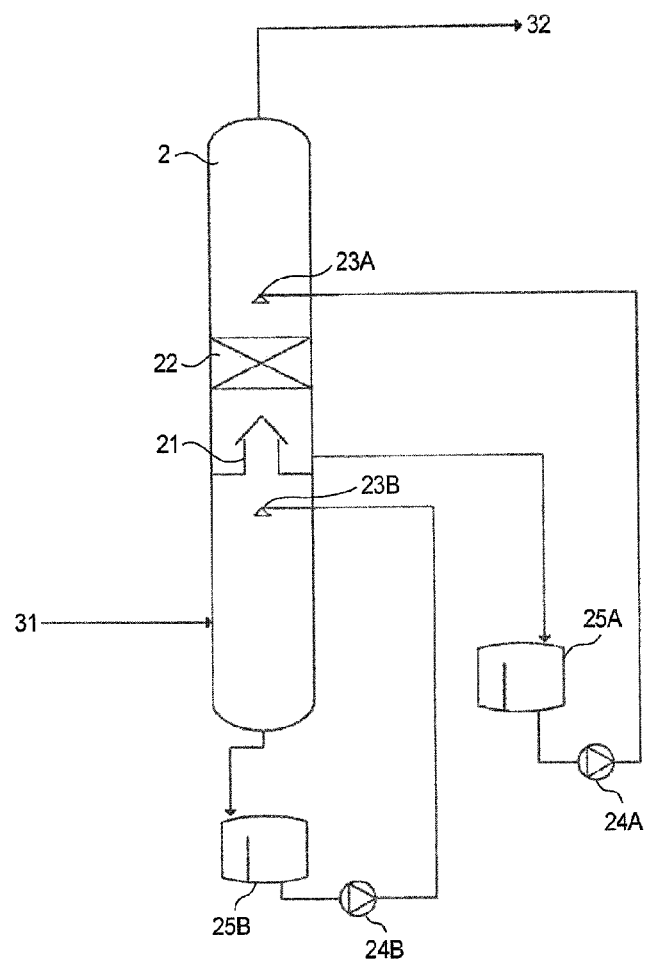
FIG. 2 is a diagram schematically illustrating an example of the quenching tower used in the method for producing the conjugated diolefin according to the present embodiment.

Since the quenching tower 2 illustrated in FIG. 2 is the same as the example illustrated in FIG. 1, except for having a decanter provided in the quenching agent circulation path and for using two types of quenching agent, in the following only the differences will be described. An organic amine aqueous solution is sprayed from the spray apparatus 23A, and an aromatic solvent is sprayed from the spray apparatus 23B. The quenching agent that has accumulated on a tray arranged integrally on the chimney 21 and at the bottom of the tower passes along the circulation path and flows into decanters 25A and 25B, respectively. In the quenching tower 2 illustrated in FIG. 2, two types of quenching agent are used. The quenching agent flowing into the circulation path includes an aqueous phase and an oil phase, which are separated by the decanters 25A and 25B. The outlet of the decanters are set so that the aqueous phase organic amine aqueous solution is fed to the spray apparatus 23A and the oil phase aromatic solvent is fed to the spray apparatus 23B.

Figure 3:
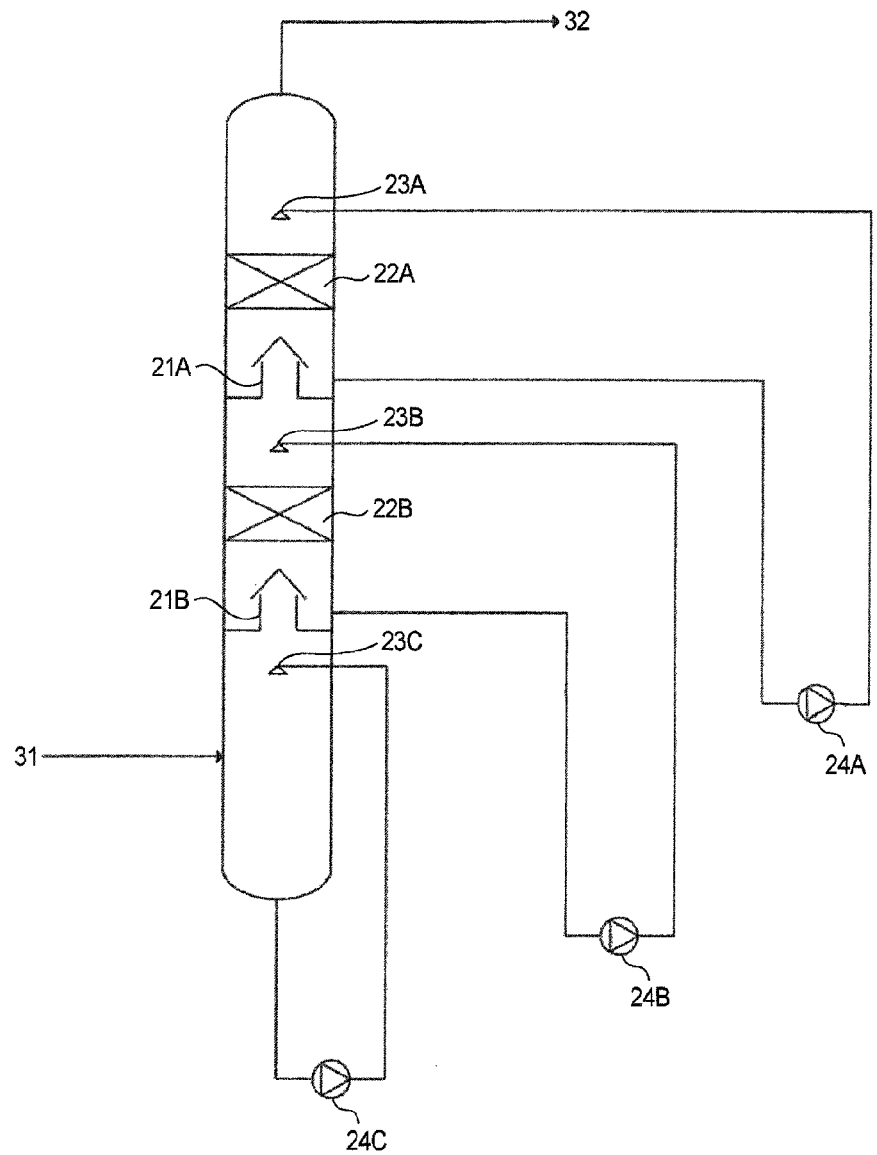
FIG. 3 is a diagram schematically illustrating an example of the quenching tower used in the method for producing the conjugated diolefin according to the present embodiment.

The quenching tower 2 illustrated in FIG. 3 is the same as the example illustrated in FIG. 1, except for having two chimneys and two packed beds, and having three sections, in which the spray apparatuses 23A and 23B are provided above packed beds 22A and 22B, respectively, and a spray apparatus 23C is provided below a chimney 21B. The organic amine aqueous solution fed from the respective spray apparatuses contacts with the gas in the tower, is then recovered on a tray arranged integrally on a chimney 21A, a tray arranged integrally on the chimney 21B, and at the bottom of the tower, goes through the circulation paths, and is returned to the respective spray apparatus 23A, 23B, and 23C.

Figure 4:
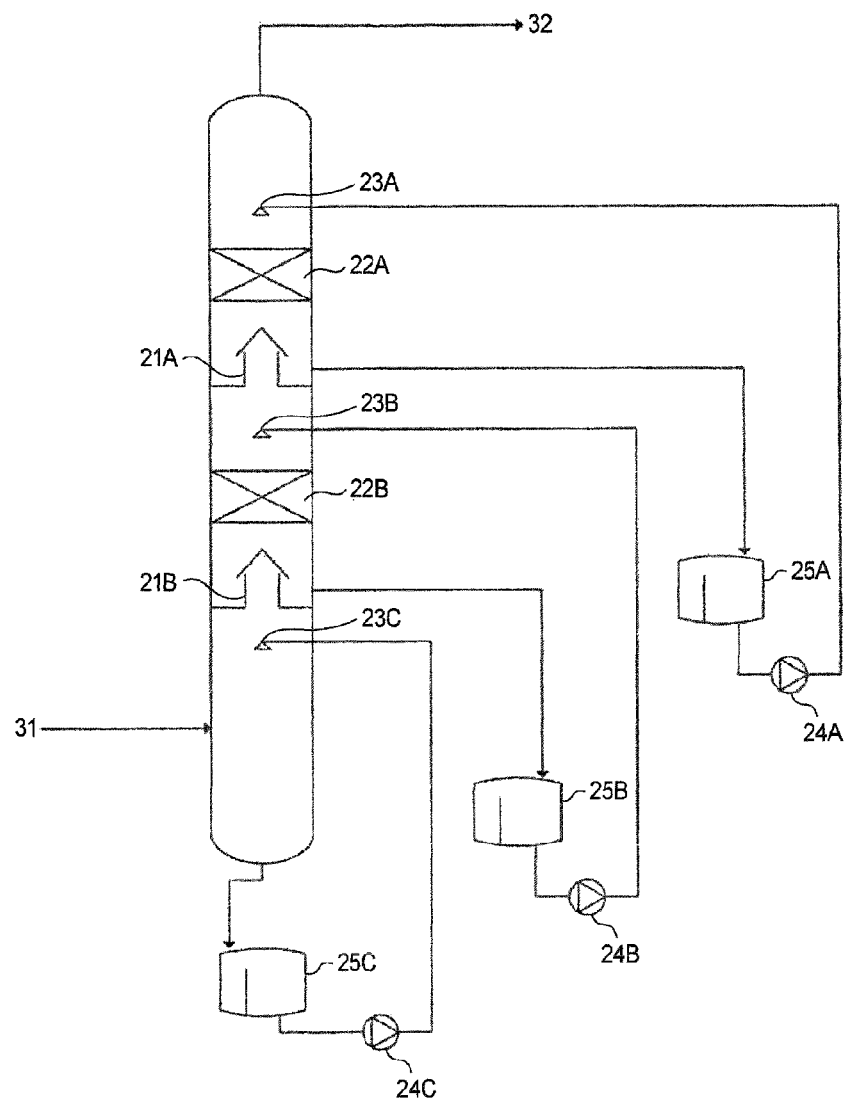
FIG. 4 is a diagram schematically illustrating an example of the quenching tower used in the method for producing the conjugated diolefin according to the present embodiment.

The quenching tower 2 illustrated in FIG. 4 is the same as that illustrated in FIG. 3, except for having a decanter provided in each circulation path and for using two types of quenching agent. An organic amine aqueous solution is fed from the spray apparatuses 23A and 23B, and an aromatic solvent is fed from the spray apparatus 23C. The quenching agents fed from the respective spray apparatuses are recovered on a tray arranged integrally on the chimney 21A, a tray arranged integrally on the chimney 21B, and at the bottom of the tower, and are then separated into an oil phase and an aqueous phase by decanters 25A, 25B and 25C provided in the respective circulation paths. The outlet of the decanters is set so that the organic amine aqueous solution is fed to the spray apparatuses 23A and 23B, and the aromatic solvent is fed to the spray apparatus 23C.

When the quenching tower has a plurality of vertical sections, and an organic amine aqueous solution and an aromatic solvent are used in combination as quenching agents, it is preferred to use the aromatic solvent as the quenching agent at the lowest section among the plurality of sections, and the organic amine aqueous solution as the quenching agent at the sections above the lowest section. When using an aromatic solvent as the quenching agent, the reaction byproducts are removed by dissolving them in the aromatic solvent. Therefore, if the used aromatic solvent is subjected to vapor distillation or the like, it can be reused. Consequently, overall production costs can be reduced, which is advantageous. On the other hand, when an organic amine aqueous solution is used as the quenching agent, the reaction byproducts are removed by reacting them with the organic amine. Therefore, unlike an aromatic solvent, it is difficult to reuse the organic amine aqueous solution by separating the organic amine aqueous solution and the byproducts. When the quenching tower has a plurality of vertical sections, the amount of reaction byproducts is usually at a maximum when the product gas by reaction is introduced into the bottom of the quenching tower, and thereafter decreases as the reaction byproducts are removed as they pass upward through each section. Therefore, when using an organic amine aqueous solution and an aromatic solvent in combination as quenching agents, from the perspective of quenching agent cost, it is advantageous to select a reusable aromatic solvent as the quenching agent for the lowest section that first comes into contact with the product gas by reaction. Based on the above, for a typical quenching tower that has a plurality of vertical sections into which the product gas by reaction is introduced from the bottom side of the quenching tower, from a cost perspective, a preferred mode is to use the aromatic solvent as the quenching agent for the lowest stage, remove the reaction byproducts included in a comparatively large amount by dissolving them in the aromatic solvent, and then remove the remaining byproducts by reacting them with the organic amine aqueous solution. Further, in the quenching tower illustrated in FIG. 4, the aromatic solvent can also be sprayed from either of the spray apparatuses 23A and 23B by changing the inlet of the decanters 25A and 25B.

Figure 5:
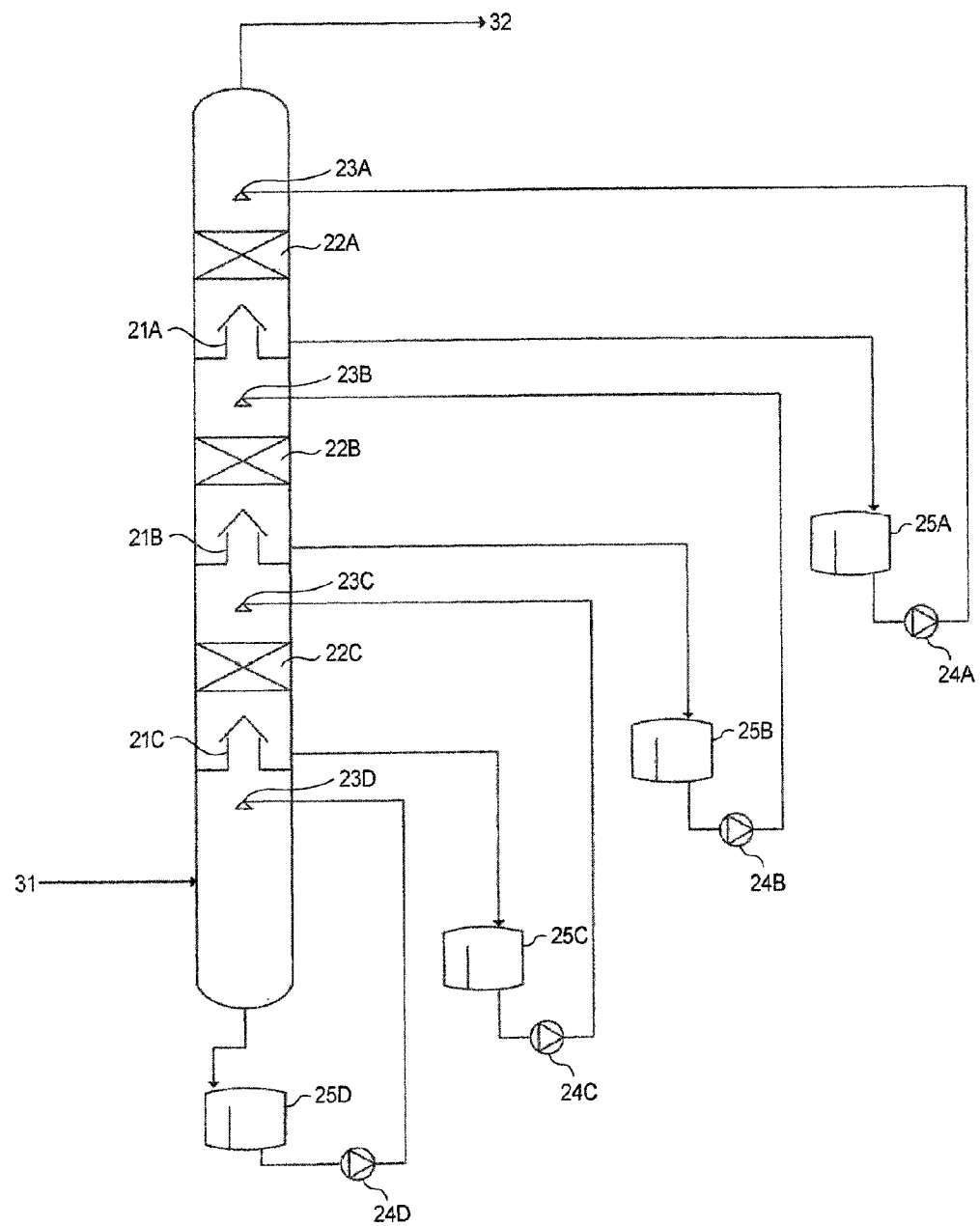
FIG. 5 is a diagram schematically illustrating an example of the quenching tower used in the method for producing the conjugated diolefin according to the present embodiment.

The quenching tower 2 illustrated in FIG. 5 is the same as the example illustrated in FIG. 4, except for having three chimneys and three packed beds, and having four sections with four spray apparatuses. In the example illustrated in FIG. 5, the organic amine aqueous solution is fed from the spray apparatuses 23A, 23B, and 23C, and the aromatic solvent is fed from a spray apparatus 23D. The aromatic solvent can also be sprayed from any of the spray apparatuses 23A, 23B, and 23C by changing the inlet of decanters 25A, 25B, and 25C arranged in the respective circulation paths.

In FIGS. 1 to 5, although a replenishment pipe for a fresh quenching agent and a discharge pipe for the quenching agent, such as the organic amine aqueous solution, and a cooling means arranged before the spray apparatus are omitted, these means may be provided as necessary.

(5) Purification Step

The product gas by reaction running out from the quenching tower can be purified based on a known technique, such as methods described in Japanese Patent Publication No. 45-17407, Japanese Patent Laid-Open No. 60-126235, Japanese Patent Publication No. 3-48891, Synthetic Rubber Handbook (pp. 92 to 100, 1969), and PETROTECH, Vol. 2, No. 4 (pp. 59 to 65, 1978), for example. For example, gas runs out from the top of a quenching tower can be introduced into the butadiene extractive distillation column described in the Synthetic Rubber Handbook, the butadiene and the butane/butenes separated, then the components with high boiling point, such as 2-butene, removed with a butadiene purification tower, and product butadiene recovered. At this point, it is preferred to purify so that the product butadiene has a purity of 98.0% or more, and preferably of 99.0% or more.

(6) Butadiene Polymerization Step

Next, a step for polymerizing polybutadiene from butadiene when butadiene is produced as the conjugated diolefin will be described.

A known method can be used for the butadiene polymerization, and solution polymerization and bulk polymerization can be carried out. For solution polymerization, the polymerization is carried out by charging a polymerization solvent and butadiene monomer into a polymerization reactor, adjusting to a predetermined temperature, and adding a polymerization initiator. Examples of the polymerization initiator include alkyl lithium compounds, such as ethyl lithium, n-propyl lithium, isopropyl lithium, n-butyl lithium, sec-butyl lithium, tert-butyl lithium, tert-octyl lithium, n-decyl lithium, phenyl lithium, 2-naphthyl lithium, 2-butyl-phenyl lithium, 4-phenyl-butyl lithium, cyclohexyl lithium, and cyclopentyl lithium. A preferred polymerization initiator is n-butyl lithium. As the polymerization solvent, any known solvent may be used. Examples include, but are not limited to, aromatic solvents such as toluene, xylene and tetralin, aliphatic and alicyclic solvents such as n-hexane, n-pentane, n-heptane, cyclohexane, cyclopentane, cycloheptane, and decalin, and the like. The polymerization temperature is about −10° C. to 150° C. The polymerization time can be appropriately set based on the temperature and the target molecular weight.

If an alkyl lithium is used for the polymerization initiator, and an aprotic hydrocarbon, such as toluene, n-hexane, and cyclohexane, is used for the polymerization solvent, living anionic polymerization proceeds with the state of the alkyl lithium being maintained also in the polymer ends. In living anionic polymerization, a polymer can be obtained that has a narrow molecular weight distribution and excellent mechanical physical properties, processability and the like. When performing living anionic polymerization of butadiene, if 4-methyl-4-formyl-1-cyclohexene and methacrolein are present, in addition to deactivation of the polymerization initiator, the polymer ends are deactivated due to a nucleophilic addition reaction on the carbonyl groups of the 4-methyl-4-formyl-1-cyclohexene and methacrolein of the polybutadiene polymer ends, whereby the polymerization reaction is terminated. This leads to the problems of an expansion in the molecular weight distribution due to an increase in low molecular weight monomers having a low degree of polymerization, specifically, deterioration of the mechanical physical properties, processability and the like when used in a synthetic rubber, resin and the like, and of an increased burden in the solvent recycling step due to an increase in unreacted butadiene in the polymerization solvent. A living polymer has the characteristic that it can undergo block polymerization with another polymer by a coupling reaction after polymerization. However, this characteristic is obviously also lost if the polymer ends are deactivated.

The polymerization reaction is terminated by adding a solvent such as an alcohol or a solvent including a polymerization inhibitor into the polymerization reactor, and stirring. The polybutadiene after completion of polymerization can be recovered by reprecipitation from the solution in the vessel using a poor solvent for polybutadiene, filtering off the precipitates, and then drying the precipitates, or by removing the solvent from the solution. The molecular weight (the weight average molecular weight Mw and number average molecular weight Mn) and the molecular weight distribution (Mw/Mn) of the recovered polybutadiene are measured using GPC (gel permeation chromatography). As the GPC mobile phase, tetrahydrofuran (THF), o-dichlorobenzene and the like can be used.

[2] Catalyst (1) Structure

As the catalyst used in the present embodiment, for example, a catalyst which comprises a metal oxide represented by the following experimental formula and a carrier can be used.

$$Mo_{12}Bi_pFe_qA_aB_bC_cD_dE_eO_x \quad \text{[Experimental formula]}$$

(wherein A represents at least one element selected from the group consisting of nickel and cobalt; B represents at least one element selected from the group consisting of alkali metal elements; C represents at least one element selected from the group consisting of magnesium, calcium, strontium, barium, zinc, and manganese; D represents at least one element selected from the group consisting of rare earth elements; E represents at least one element selected from the group consisting of chromium, indium, and gallium; O represents oxygen; p, q, a, b, c, d, e, and x denote an atomic ratio of bismuth, iron, A, B, C, D, E, and O, respectively, to 12 molybdenum atoms, where $0.1 \leq p \leq 5$, $0.5 \leq q \leq 8$, $0 \leq a \leq 10$, $0.02 \leq b \leq 2$, $0 \leq c \leq 5$, $0 \leq d \leq 5$, and $0 \leq e \leq 5$; and x denotes the number of oxygen atoms required to satisfy valence requirements of other elements that are present.)

The expression "experimental formula" used herein represents the atomic ratios of the metals included in the formula and the composition of the required oxygen based on the sum of those atomic ratios and the oxidation numbers. In an oxide containing metals that can have various oxidation numbers, since it is essentially impossible to specify the number of oxygen atoms, the number of oxygen is formally denoted as "x". For example, when obtaining an oxide by preparing a slurry that includes a Mo compound, a Bi compound, and an Fe compound, and drying and/or baking the slurry, the atomic ratio of the metals included in the slurry and the atomic ratio of the metals in the obtained oxide can be thought to be essentially the same. Therefore, the formula obtained by adding $O_x$ to the charging composition formula of the slurry is the experimental formula of the obtained oxide. Further, in the present specification, like the above-described charging composition of the slurry, the formula representing the intentionally controlled components and the ratios thereof is also referred to as "composition formula". Therefore, in the above-described example, the formula obtained by taking away $O_x$ from the experimental formula is the "composition formula".

Although the role of the arbitrary components represented as A, B, C, D, and E is not limited, in the field of oxide catalysts having Mo, Bi, and Fe as essential components, the role of these arbitrary components can basically be thought as follows. Specifically, A and E improve catalytic activity, B and C stabilize the structure of the oxide for the purpose that contains Mo, Bi, and Fe, and D has an effect of re-oxidizing the oxide. If p, q, a, b, c, d, and e are in the preferred range, these effects can be expected to be much greater.

In the above-described composition formula, a more preferred composition is $0.1 \leq p \leq 0.5$, $1.5 \leq q \leq 3.5$, $1.7 \leq a \leq 9.0$, $0.02 \leq b \leq 0.5$, $0.5 \leq c \leq 4.5$, $0.02 \leq d \leq 0.5$, and $0 \leq e \leq 4.5$, and in an even more preferred composition, B is rubidium, potassium, or cesium, C is magnesium, and D is cerium, and $0.15 \leq p \leq 0.4$, $1.7 \leq q \leq 3.0$, $2.0 \leq a \leq 8.0$, $0.03 \leq b \leq 0.3$, $1.0 \leq c \leq 3.5$, $0.05 \leq d \leq 0.3$, and $0 \leq e \leq 3.5$. If A is nickel, B is rubidium, potassium, or cesium, C is magnesium, and D is cerium, the conjugated diolefin yield tends to be higher, and the catalyst can usually be conferred with resistance to reductive degradation.

The carrier can be effectively used in a range of, based on a total of the carrier and the oxide, preferably 30 to 70% by weight, and more preferably 40 to 60% by weight. A catalyst comprising a metal oxide that contains Mo, Bi, and Fe can be obtained by a known method, such as a method that includes a first step of preparing a raw material slurry, a second step of spray drying the raw material slurry, and a third step of baking the dried product obtained from the second step. The carrier is preferably silica, alumina, titania, or zirconia. Silica is more preferred as the carrier. Compared with other carriers, silica has a lower activity, and has an effect of bonding well with the catalyst without causing the activity or the selectivity of the catalyst with respect to the target product to deteriorate. Further, by supporting an oxide on a carrier, good physical properties that are especially suited to use in a fluidized bed reaction, such as particle shape/size/distribution, fluidity, and mechanical strength can be obtained.

(2) Production Method

A preferred mode of the method for producing the catalyst, which includes a first step of preparing a raw material slurry, a second step of spray drying the raw material slurry, and a third step of calcined the dried product obtained from the second step, will now be described.

In the first step, a raw material slurry is obtained by preparing the catalyst raw materials. Examples of the elemental source for the respective elements of molybdenum, bismuth, iron, nickel, cobalt, alkali metal elements, magnesium, calcium, strontium, barium, zinc, manganese, rare earth elements, chromium, indium, and gallium include an ammonium salt, nitrate, hydrochloride, sulfate, organic acid salt and the like that are soluble in water or nitric acid. Especially, as the elemental source for the respective elements, an ammonium salt is preferred as the molybdenum source, and the respective nitrate is preferred for bismuth, iron, nickel, alkali elements, magnesium, zinc, manganese, and rare earth elements. As described above, an oxide, such as silica, alumina, titania, or zirconia, can be used for the oxide carrier. It is preferred to use silica as the carrier, and to use a silica sol for the silica source. Regarding impurities in the silica sol, it is preferred to use a silica sol containing not more than 0.04 aluminum atoms per 100 atoms of silicon, and more preferably a silica sol containing not more than 0.02 aluminum atoms per 100 atoms of silicon. Preparation of the raw material slurry can be carried out by adding an ammonium salt of molybdenum that has been dissolved in water to a silica sol, and then adding a solution obtained by dissolving a nitrate of the respective elements of bismuth, a rare earth element, iron, nickel, magnesium, zinc, manganese, and an alkali element in water or aqueous nitric acid. When preparing the raw material slurry in this manner, the addition order may be changed from that described above.

In the second step, spherical particles are obtained by spray drying the raw material slurry obtained from the first step. Atomization of the raw material slurry can be carried out by a method commonly performed industrially, such as a centrifugal method, a two-fluid nozzle method, and a high-pressure nozzle method. It is especially preferred to perform the atomization of the raw material slurry using a centrifugal method. Next, the obtained particles are dried. As the drying heat source, it is preferred to use steam or air heated with an electric heater and the like. The temperature of the drier inlet is 100 to 400° C., and preferably 150 to 300° C.

In the third step, the desired catalyst is obtained by calcining the dry particles obtained from the second step. It is preferred to dry the particles at 150 to 500° C. as necessary, and then calcining for 1 to 20 hours in a temperature range of at 500 to 700° C., and preferably a temperature range of 550 to 700° C. The calcination can be carried out using a calcining furnace, such as a rotary furnace, a tunnel furnace, and a muffle furnace.

It is preferred that the catalyst has a particle size distribution in the range of 10 to 150 μm.

[3] Conjugated Diolefin Production Apparatus

The apparatus for the conjugated diolefin production according to the present embodiment has:
  a reactor accommodated with a catalyst which comprises a metal oxide and a carrier; and
  a quenching tower connected to the reactor.

This production apparatus can be preferably used in the above-described method for producing a conjugated diolefin. Specifically, a hydrocarbon containing a monoolefin that has 4 or more carbon atoms and oxygen is fed into a reactor in the above-described production apparatus, a product gas by reaction containing a conjugated diolefin thus produced flows into the above-described quenching tower, and is washed with a quenching agent in the quenching tower. It is preferred to use an organic amine aqueous solution as the quenching agent, and to also use an aromatic organic solvent in combination.

A preferred mode of the apparatus for the conjugated diolefin production according to the present embodiment will now be described with reference to FIGS. 6 and 7.

Figure 6:
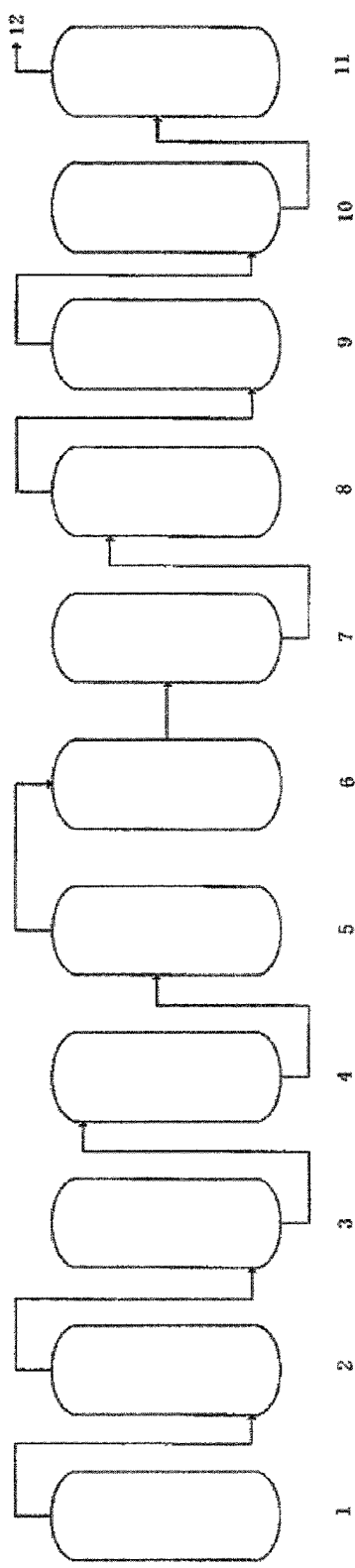
FIG. 6 is a diagram schematically illustrating an example of an apparatus for a conjugated diolefin production according to the present embodiment.

FIG. 6 is a diagram schematically illustrating an example of an apparatus for a conjugated diolefin production according to the present embodiment. The product gas by reaction running out from the reactor is sent from the bottom of the quenching tower to a quenching section, and is washed in the quenching tower by coming into contact with an organic amine aqueous solution or an organic amine aqueous solution and an aromatic solvent. The washed product gas by reaction runs out from the top of the tower, and is introduced into the bottom of an absorption tower. The product gas by reaction introduced into the bottom of the absorption tower is absorbed by a solvent (e.g., xylene, a mixed xylene, or toluene) in the absorption tower, and runs out from the bottom of the tower as a conjugated diolefin-containing solution. On the other hand, an off-gas runs out from the top of the absorption tower. The conjugated diolefin-containing solution withdrawn from the bottom of the absorption tower is introduced into an upper portion of a stabilizer. If an inert gas is included in the raw material components, the inert gas is separated from the conjugated diolefin-containing solution at the stabilizer. The conjugated diolefin-containing solution from which the inert gas has been separated is stripped from the bottom of the stabilizer, and is introduced into a flash tower. The solvent is separated from the conjugated diolefin-containing solution at the flash tower. Then, a solution including the conjugated diolefin and water runs out from the top of the tower, and is fed to a condenser. The water is separated from the solution by the condenser to obtain a crude conjugated diolefin. This crude conjugated diolefin is fed to a middle stage of a first extractive distillation column. A solvent (e.g., dimethylformamide) is sprayed from the top of the first extractive distillation column to produce a solution of the crude conjugated diolefin, which is withdrawn from the bottom of the column. The distilled crude conjugated diolefin solution is introduced into a stripping tower, where butane, for example, is separated from the top of the tower. The solvent in the crude conjugated diolefin solution is separated at the stripping tower, and crude conjugated diolefin stripped from the top of the tower is introduced into a second extractive distillation column. At the second extractive distillation column too, a solvent is similarly sprayed from the top of the column like at the first extractive distillation column, to produce a crude conjugated diolefin solution. The second extractive distillation column is operated at a temperature at which the component including the conjugated diolefin is distilled from the top of the column, and the solvent in which impurities, such as acetylenes, are dissolved is separated from the bottom of the column. Consequently, the crude conjugated diolefin is distilled from the top of the second extractive distillation column. When the low boiling point compounds (e.g., methyl acetylene) and compounds with high boiling point (e.g., 2-butene) are separated at the first and the second extractive distillation columns from the crude conjugated diolefin distilled from the second extractive distillation column, a purified conjugated diolefin is obtained.

Figure 7:
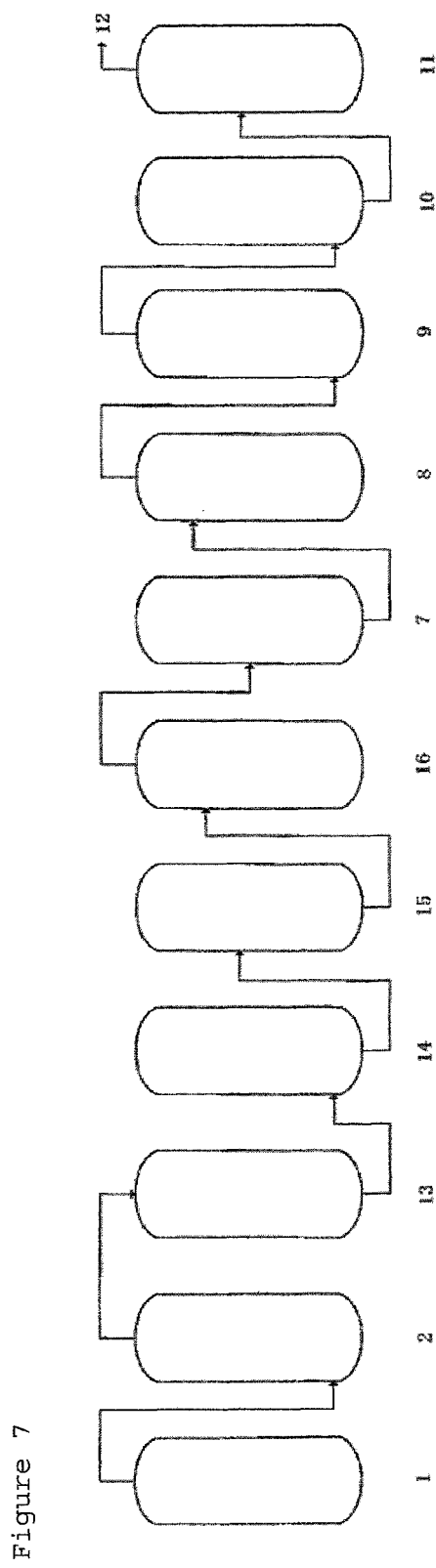
FIG. 7 is a diagram schematically illustrating another example of a conjugated diolefin production apparatus according to the present embodiment.

FIG. 7 is a diagram schematically illustrating another example of an apparatus for a conjugated diolefin production according to the present embodiment. Since the reactor, the quenching tower, and the towers/columns after the first extractive distillation column in the apparatus illustrated in FIG. 7 are the same as the example illustrated in FIG. 6, only the differences will be described here. The product gas by reaction washed at the quenching tower is introduced into a dewatering tower packed with a dewatering agent, such as molecular sieves, withdrawn from the bottom of the tower, and fed to a solvent absorption tower. The product gas by reaction comes into contact with a solvent that is sprayed by the solvent absorption tower to produce a conjugated diolefin-containing solution. The produced conjugated diolefin-containing solution is withdrawn from the bottom of the tower, and is introduced into a degassing tower and a solvent separation column. If an inert gas is included in the raw material components, the inert gas is separated from the conjugated diolefin-containing solution at the degassing tower. Further, the solvent is separated from the conjugated diolefin-containing solution at the solvent separation column, whereby a crude conjugated diolefin is obtained.

Further, in the examples illustrated in FIGS. 6 and 7, although description of a compressor, a drain pot, a heat-exchanger and the like is omitted, these parts may be appropriately added based on operational necessity or efficiency in the apparatus, or to effectively utilize heat, for example. For example, referring to the apparatuses described in Japanese Patent Laid-Open Nos. 60-193931, 2003-128595, and 2010-90082 is effective when adding a compressor, drain pot, heat exchanger and the like. Further, these documents can also be referred to from the perspective of operation temperature and pressure of the distillation columns, and the type of solvent, for example.

EXAMPLES

The present invention will now be described in more detail based on the following Examples. However, the present invention is not limited to the below-described Examples.
(Reaction Results)

In Examples and Comparative Examples, the n-butene conversion ratio, and the 1,3-butadiene selectivity and yield were defined based on the following equations to illustrate the reaction results.

$$n\text{-Butene Conversion Ratio (\%)} = \frac{\text{(Number of Moles of Reacted } n\text{-Butene)}}{\text{(Number of Moles of Fed } n\text{-Butene)}} \times 100 \quad \text{[Equation 2]}$$

$$\text{Butadiene Selectivity (\%)} = \frac{\text{(Number of Moles of Produced Butadiene)}}{\text{(Number of Moles of Reacted } n\text{-Butene)}} \times 100 \quad \text{[Equation 3]}$$

$$\text{Butadiene Yield (\%)} = \frac{\text{(Number of Moles of Produced Butadiene)}}{\text{(Number of Moles of Fed } n\text{-Butene)}} \times 100 \quad \text{[Equation 4]}$$

(Reaction Apparatus)
As the fluidized bed type reaction apparatus, a fluidized bed reactor made from SUS304 having a 3 inch pipe diameter and a height of 95 mm was used.
(Raw Material Mixed Gas)
A raw material mixed gas with a composition in a molar ratio of BBSS/air/nitrogen of 1/2 to 12/97 to 87/balance was fed to the reaction apparatus at a flow rate F of 500 to 2,500 NL/hr (based on NTP). The used BBSS had a C4 component composition of 1-butene:2-trans-butene:2-cis-butene:isobutene:n-butane:isobutane:butadiene=41.3:17.7:13.5:5.6:16.1:4.7:1.1.
(Reaction Conditions)
The reaction was carried out under conditions of a reaction temperature T of 325 to 370° C., reaction pressure P of 0.05 MPaG, and catalyst weight W of 1,200 g.
(Contact Time)
The contact time was defined based on the following equation.

$$\text{Contact Time (g·sec/cc)} = \frac{w \times 3.6 \times 273.15 \times (P \times 1000 + 101.325)}{F \times (273.15 + T) \times 101.325} \quad \text{[Equation 5]}$$

wherein W represents the amount of a catalyst (g), F represents the flow rate of a raw material mixed gas (NL/hr, based on NTP), T represents the reaction temperature (° C.), and P represents the reaction pressure (MPaG).
(Analysis of Product Gas by Reaction)
Analysis of the product gas by reaction was carried out using a gas chromatography apparatus directly connected to the fluidized bed reactor (GC-2010 (manufactured by Shimadzu Corporation), analysis column: HP-ALS (manufactured by Agilent Technologies, Inc.), carrier gas: helium, column temperature: after gas injection, holding for 8 minutes at 100° C., then increasing temperature to 195° C. at 10°

C./min, and then holding for 40 minutes at 195° C., TCD (thermal conduction detector)/FID (hydrogen flame ionization detector) set temperature: 250° C.)

(Quenching Tower)

As the quenching tower, a quenching tower made from SUS304 having a can portion (tower bottom) with a pipe diameter of 200 mm and a height of 300 mm and a tower portion (quenching portion) with a pipe diameter of 100 mm and a height of 1,000 mm above the can portion was used. The quenching portion was divided into three stages, in which a liquid withdrawn from the tower bottom was sprayed at an upper stage, a middle stage, and a lower stage at, except for the following cases, 100, 170, and 160 L/Hr, respectively.

(Analysis of Liquid at Bottom of Quenching Tower)

Analysis of the liquid at the bottom of the quenching tower was carried out in the following two ways.

(1) Using a gas chromatography apparatus (GC-2010 (manufactured by Shimadzu Corporation), analysis column: CP-Volamine (manufactured by Varian Inc.), carrier gas: helium, column temperature: after holding for 10 minutes at 40° C., then increasing temperature to 300° C. at 10° C./min and holding, FID (hydrogen flame ionization detector) set temperature: 250° C.), the analysis was carried out.

(2) Using a gas chromatography mass spectrometer (GCMS-QP2010 Plus (manufactured by Shimadzu Corporation), GC analysis column: DB-WAX (manufactured by Agilent Technologies, Inc.), carrier gas: helium, column temperature: after gas injection, holding for 11 minutes at 60° C., then increasing temperature to 135° C. at 7.5° C./min, followed by increasing temperature to 250° C. at 11.5° C./min, and holding for 20 minutes, ionization mode: electron ionization (EI) MS ion source temperature: 200° C., and MS sample chamber temperature: 250° C.), the analysis was carried out.

(Polybutadiene Analysis)

Analysis of polybutadiene was carried out using a gel permeation chromatography apparatus (GPC-8020 (manufactured by Tosoh Corporation) with tetrahydrofuran (THF) as the mobile phase) to determine the molecular weight (Mw and Mn based on standard polystyrene) and Mw/Mn at a measurement temperature of 40° C.

Example 1

(a) Preparation of Catalyst

A catalyst was prepared in the following manner by supporting an oxide having a composition represented by $Mo_{12}Bi_{0.60}Fe_{1.8}Ni_{5.0}K_{0.09}Rb_{0.05}Mg_{2.0}Ce_{0.75}$ on 50% by weight of silica. To 3,000 g of a silica sol containing 30% by weight of $SiO_2$, a solution obtained by dissolving 95.9 g of bismuth nitrate [$Bi(NO_3)_3.5H_2O$], 107.4 g of cerium nitrate [$Ce(NO_3)_3.6H_2O$], 239.8 g of iron nitrate [$Fe(NO_3)_3.9H_2O$], 479.6 g of nickel nitrate [$Ni(NO_3)_2.6H_2O$], 169.2 g of magnesium nitrate [$Mg(NO_3)_2.6H_2O$], 2.9 g of potassium nitrate [$KNO_3$], and 2.5 g of rubidium nitrate [$RbNO_3$] in 675.5 g of 16.6% by weight nitric acid. Lastly, to the mixture, a solution obtained by dissolving 698.6 g of ammonium paramolybdate [$(NH_4)_6Mo_7O_{24}.4H_2O$] in 1,407.2 ml of water was added. The resultant raw material preparation was sent to a parallel-flow spray drier, and dried at an inlet temperature of about 250° C. and an outlet temperature of about 140° C. The preparation was atomized using an atomization apparatus equipped with a dish-shaped rotor arranged in the middle of the upper portion of the drier. The obtained powder was precalcined for 1 hour at 350° C. under an air atmosphere in an electric furnace, then calcined for 2 hours at 590° C. under an air atmosphere to obtain the catalyst.

(b) Butadiene Production Reaction 1,200 g of the catalyst obtained in the above-described catalyst preparation step (a) was charged into an SUS304 fluidized bed reactor having a 3 inch pipe diameter and a height of 950 mm. A raw material gas (n-butene concentration of 7% by volume) with a composition in a molar ratio of BBSS/air/nitrogen of 1/3.7/95.3/balance was fed to the reactor at a flow rate F of 920 NL/hr (based on NTP), and a reaction was carried out under conditions of a reaction temperature T of 360° C. and a reaction pressure P of 0.05 MPaG to obtain a product gas by reaction. The contact time between the catalyst and the raw material gas was 3.0 (g·sec/cc). The BBSS used for a raw material had a C4 component composition of 1-butene:2-trans-butene:2-cis-butene:isobutene:n-butane:isobutane:butadiene=41.3:17.7:13.5:5.6:16.1:4.7:1.1.

Analysis of the product gas by reaction was carried out as described above using a gas chromatography apparatus directly connected to the reactor and a quenching tower. The reaction results 24 hours after the reaction started were an n-butene conversion ratio of 95.5%, a butadiene selectivity of 83.1%, and a butadiene yield of 79.4%.

(c) Quenching of Product Gas by Reaction

The product gas by reaction obtained in the above step (b) was introduced into a lower stage of a quenching tower (made from SUS304 having a quenching unit (tube diameter 100 mm, height 1,000 mm) on an upper portion of the bottom (tube diameter 200 mm, height 300 mm)). An aqueous solution of 25% by weight monoethanolamine was sprayed as a quenching agent from an upper stage of the quenching tower at 500 L/hr, and a discharge gas was obtained from the top of the quenching tower. At this point, the temperature of the discharge gas from the top of the quenching tower was 50° C. Further, the concentration of 4-methyl-4-formyl-1-cyclohexene and methacrolein in the liquid at the bottom of the quenching tower was 1,140 ppm by weight, and the concentration of benzoic acid was 133 ppm by weight. Throughout 3 months or more of operation, the pressure in the quenching tower was maintained at 0.05 MPaG, which was the same as that of the fluidized bed reactor, and there were no blockages.

(d) Purification of Butadiene

Using the apparatus illustrated in FIG. 7, the quenched discharge gas was subjected to a dewatering step, a recovery step, a degassing step, a butadiene separation step, and a crude butadiene purification step. More specifically, a purification apparatus was assembled in the same manner as the downstream portion from the quenching tower illustrated in FIG. 1 of Japanese Patent Laid-Open No. 2010-90082, and the discharge gas from the top of the quenching tower was subjected to separation of the condensate water, pressurization with a compressor, and re-cooling and water separation. Then, the resultant product was introduced into a dewatering tower packed with molecular sieves. The dewatered gas was introduced into a recovery tower, and then subjected to counter-current contact with dimethylformamide set at a liquid temperature of 30 to 40° C. The obtained butadiene solution was purified by introducing it into an extractive distillation column to obtain butadiene having a purity of 99.3%.

(e) Polymerization of Butadiene

A 1.5 L autoclave that had been purged with nitrogen was charged with 50 g of the butadiene obtained in the above-described step (d), 200 g of cyclohexane, 0.556 mmol of n-butyl lithium, and 0.1 mol/L THF, and polymerization was carried out for 1 hour at 70° C. to obtain polybutadiene. After polymerization finished, the toluene was removed and the polybutadiene was recovered. Determination of the molecular weight showed that Mw was 216,000, Mn was 202,000, and Mw/Mn of 1.07.

Example 2

Butadiene production, quenching of the product gas by reaction, and butadiene purification were carried out in the same manner as in Example 1, except that an aqueous solution of 25% by weight diethanolamine was used as the quenching agent of the product gas by reaction in the step (c).

Throughout operation the pressure in the quenching tower was maintained at 0.05 MPaG, which was the same as that of the fluidized bed reactor, and there were no blockages. At this point, the concentration of 4-methyl-4-formyl-1-cyclohexene and methacrolein in the liquid at the bottom of the quenching tower was 834 ppm by weight, the concentration of benzoic acid was 76 ppm by weight, and butadiene having a purity of 99.3% was obtained. The molecular weight of the polybutadiene obtained by polymerizing this butadiene in the same manner as in Example 1 was Mw of 213,000, Mn of 197,000, and Mw/Mn of 1.08.

Example 3

Butadiene production, quenching of the product gas by reaction, and butadiene purification were carried out in the same manner as in Example 1, except that an aqueous solution of 25% by weight triethanolamine was used as the quenching agent of the product gas by reaction in the step (c). Throughout operation the pressure in the quenching tower was maintained at 0.05 MPaG, which was the same as that of the fluidized bed reactor, and there were no blockages. At this point, the concentration of 4-methyl-4-formyl-1-cyclohexene and methacrolein in the liquid at the bottom of the quenching tower was 787 ppm by weight, the concentration of benzoic acid was 55 ppm by weight, and butadiene having a purity of 99.3% was obtained. The molecular weight of the polybutadiene obtained by polymerizing this butadiene in the same manner as in Example 1 was Mw of 214,000, Mn of 198,000, and Mw/Mn of 1.08.

Comparative Example 1

Butadiene production, quenching of the product gas by reaction, and butadiene purification were carried out in the same manner as in Example 1, except that water was used as the quenching agent of the product gas by reaction in the step (c). During operation the pressure in the quenching tower increased over time. When the pressure reached 0.09 MPaG, an open inspection was carried out, whereby blockages were found in the top of the quenching tower. At this point, the concentration of 4-methyl-4-formyl-1-cyclohexene and methacrolein in the liquid at the bottom of the quenching tower was 130 ppm by weight, benzoic acid was not detected, and butadiene having a purity of 99.0% was obtained. The molecular weight of the polybutadiene obtained by polymerizing this butadiene in the same manner as in Example 1 was Mw of 192,000, Mn of 109,000, and Mw/Mn of 1.76.

Comparative Example 2

Butadiene production, quenching of the product gas by reaction, and butadiene purification were carried out in the same manner as in Example 1, except that 25% by weight of sodium hydroxide aqueous solution was used as the quenching agent of the product gas by reaction in the step (c). During operation the pressure in the quenching tower increased over time. When the pressure reached 0.08 MPaG, an open inspection was carried out, whereby blockages were found in the top of the quenching tower. At this point, the concentration of 4-methyl-4-formyl-1-cyclohexene and methacrolein in the liquid at the bottom of the quenching tower was 317 ppm by weight, the concentration of benzoic acid was 70 ppm by weight, and butadiene having a purity of 99.0% was obtained. The molecular weight of the polybutadiene obtained by polymerizing this butadiene in the same manner as in Example 1 was Mw of 198,000, Mn of 139,000, and Mw/Mn of 1.42.

Example 4

Butadiene production, quenching of the product gas by reaction, and butadiene purification were carried out in the same manner as in Example 1, except that BBSS having a C4 component composition of 1-butene:2-trans-butene:2-cis-butene:isobutene:n-butane:isobutane:butadiene=42.6:18.3:13.9:2.5:16.6:4.9:1.1 was used for the hydrocarbon raw material. Reaction results based on analysis of the obtained product gas by reaction 24 hours after the reaction started were an n-butene conversion ratio of 97.2%, a butadiene selectivity of 82.3%, and a butadiene yield of 80.0%.

Throughout operation the pressure in the quenching tower was maintained at 0.05 MPaG, which was the same as that of the fluidized bed reactor, and there were no blockages. At this point, the concentration of 4-methyl-4-formyl-1-cyclohexene and methacrolein in the liquid at the bottom of the quenching tower was 572 ppm by weight, and butadiene having a purity of 99.5% was obtained. The molecular weight of the polybutadiene obtained by polymerizing this butadiene in the same manner as in Example 1 was Mw of 217,000, Mn of 209,000, and Mw/Mn of 1.04.

Example 5

A catalyst was prepared in the following manner by supporting an oxide having a composition represented by $Mo_{12}Bi_5Fe_{0.35}Ni_{2.7}Co_{2.7}Na_{0.35}K_{0.1}B_{0.2}$ on 50% by weight of silica. To 3,680 g of a silica sol including 30% by weight $SiO_2$, a solution obtained by dissolving 799.7 g of bismuth nitrate, 46.6 g of iron nitrate, 258.9 g of nickel nitrate, 259.1 g of cobalt nitrate [$Co(NO_3)_2 \cdot 6H_2O$], 9.81 g of sodium nitrate [$NaNO_3$], 3.33 g of potassium nitrate, and 4.08 g of boric acid [$H_3BO_3$] in 3,600 g of 16.6% by weight nitric acid was added. Finally, to the mixture, a solution obtained by dissolving 698.6 g of ammonium paramolybdate in 1,407.2 ml of water was added. The resultant raw material preparation was dried and calcined in the same manner as in Example 1 to obtain the catalyst.

Using the obtained catalyst, butadiene production, quenching of the product gas by reaction, and butadiene purification were carried out in the same manner as in Example 1. Reaction results based on analysis of the obtained product gas by reaction 24 hours after the reaction started were an n-butene conversion ratio of 87.3%, a butadiene selectivity of 82.2%, and a butadiene yield of 71.8%.

Throughout operation the pressure in the quenching tower was maintained at 0.05 MPaG, which was the same as that of the fluidized bed reactor, and there were no blockages. At this point, the concentration of 4-methyl-4-formyl-1-cyclohexene and methacrolein in the liquid at the bottom of the quenching tower was 840 ppm by weight, and butadiene having a purity of 99.2% was obtained. The molecular weight of the polybutadiene obtained by polymerizing this butadiene in the same manner as in Example 1 was Mw of 209,000, Mn of 190,000, and Mw/Mn of 1.10.

Comparative Example 3

Butadiene production, quenching of the product gas by reaction, and butadiene purification were carried out in the same manner as in Comparative Example 2, except that the catalyst obtained in Example 5 was used. During operation the pressure in the quenching tower increased over time. When the pressure reached 0.09 MPaG, an open inspection was carried out, whereby blockages were found in the top of the quenching tower. At this point, the concentration of 4-methyl-4-formyl-1-cyclohexene and methacrolein in the liquid at the bottom of the quenching tower was 310 ppm by weight, and butadiene having a purity of 98.9% was obtained. The molecular weight of the polybutadiene obtained by polymerizing this butadiene in the same manner as in Example 1 was Mw of 201,000, Mn of 134,000, and Mw/Mn of 1.50.

Example 6

Butadiene production, quenching of the product gas by reaction, and butadiene purification were carried out in the same manner as in Example 1, except that an aqueous solution of 8% by weight monoethanolamine was used as the quenching agent of the product gas by reaction in the step (c). Throughout 2 months of operation the pressure in the quenching tower was maintained at 0.05 MPaG, which was the same as that of the fluidized bed reactor, and there were no blockages. At this point, the concentration of 4-methyl-4-formyl-1-cyclohexene and methacrolein in the liquid at the bottom of the quenching tower was 462 ppm by weight, the concentration of benzoic acid was 43 ppm by weight, and butadiene having a purity of 99.0% was obtained. The molecular weight of the polybutadiene obtained by polymerizing this butadiene in the same manner as in Example 1 was Mw of 204,000, Mn of 133,000, and Mw/Mn of 1.53.

Example 7

Butadiene production, quenching of the product gas by reaction, and butadiene purification were carried out in the same manner as in Example 1, except that an aqueous solution of 15% by weight monoethanolamine was used as the quenching agent of the product gas by reaction in the step (c). Throughout operation the pressure in the quenching tower was maintained at 0.05 MPaG, which was the same as that of the fluidized bed reactor, and there were no blockages. At this point, the concentration of 4-methyl-4-formyl-1-cyclohexene and methacrolein in the liquid at the bottom of the quenching tower was 881 ppm by weight, and butadiene having a purity of 99.3% was obtained. The molecular weight of the polybutadiene obtained by polymerizing this butadiene in the same manner as in Example 1 was Mw of 215,000, Mn of 201,000, and Mw/Mn of 1.07.

Example 8

Butadiene production, quenching of the product gas by reaction, and butadiene purification were carried out in the same manner as in Example 1, except that an aqueous solution of 80% by weight monoethanolamine was used as the quenching agent of the product gas by reaction in the step (c). Throughout operation the pressure in the quenching tower was maintained at 0.05 MPaG, which was the same as that of the fluidized bed reactor, and there were no blockages. At this point, monoethanolamine was detected in the product gas by reaction running out from the top of the quenching tower. Further, the concentration of 4-methyl-4-formyl-1-cyclohexene and methacrolein in the liquid at the bottom of the quenching tower was 1,110 ppm by weight, the concentration of benzoic acid was 311 ppm by weight, and butadiene having a purity of 99.3% was obtained. The molecular weight of the polybutadiene obtained by polymerizing this butadiene in the same manner as in Example 1 was Mw of 216,000, Mn of 201,000, and Mw/Mn of 1.07.

Example 9

Butadiene production, quenching of the product gas by reaction, and butadiene purification were carried out in the same manner as in Example 1, except that as the quenching agent of the product gas by reaction in the step (c), an aqueous solution of 25% by weight monoethanolamine was sprayed from an upper stage and a middle stage of the quenching tower at 100 L/hr and 170 L/hr, respectively, and m-xylene was sprayed from a lower stage of the quenching tower at 160 L/hr. For each of the quenching agents, the withdrawn liquid from the respective stages was recycled, and the withdrawn liquid from the respective stages was re-fed to the respective stages after the aqueous phase and the oil phase were separated. Further, in the following Examples too, when an aromatic agent was employed as a quenching gent, the withdrawn liquid was circulated after the aqueous phase and the oil phase were separated.

Throughout operation the pressure in the quenching tower was maintained at 0.05 MPaG, which was the same as that of the fluidized bed reactor, and there were no blockages. At this point, the concentration of 4-methyl-4-formyl-1-cyclohexene and methacrolein in the withdrawn liquid from the upper and middle sections of the quenching tower was 1,367 ppm by weight, the concentration of benzoic acid in the withdrawn liquid from the lower section was 2,777 ppm by weight, and butadiene having a purity of 99.4% was obtained. The molecular weight of the polybutadiene obtained by polymerizing this butadiene in the same manner as in Example 1 was Mw of 213,000, Mn of 197,000, and Mw/Mn of 1.08.

Example 10

Butadiene production, quenching of the product gas by reaction, and butadiene purification were carried out in the same manner as in Example 1, except that as the quenching agent of the product gas by reaction in the step (c), an aqueous solution of 8% by weight monoethanolamine was sprayed from an upper stage and a middle stage of the quenching tower at 100 L/hr and 170 L/hr, respectively, and m-xylene was sprayed from a lower stage of the quenching tower at 160 L/hr. Throughout operation the pressure in the quenching tower was remained at 0.05 MPaG, which was the same as that of the fluidized bed reactor, and there were no blockages. At this point, the concentration of 4-methyl-4-formyl-1-cyclohexene and methacrolein in the withdrawn liquid from the upper and middle sections of the quenching tower was 110 ppm by weight, the concentration of benzoic acid in the withdrawn liquid from the lower section was 2,828 ppm by weight, and butadiene having a purity of 99.2% was obtained. The molecular weight of the polybutadiene obtained by polymerizing this butadiene in the same manner as in Example 1 was Mw of 210,000, Mn of 194,000, and Mw/Mn of 1.08.

Example 11

Butadiene production, quenching of the product gas by reaction, and butadiene purification were carried out in the same manner as in Example 1, except that as the quenching agent of the product gas by reaction in the step (c), an aqueous solution of 80% by weight monoethanolamine was sprayed from an upper stage and a middle stage of the quenching tower at 100 L/hr and 170 L/hr, respectively, and m-xylene was sprayed as a circulating liquid from a lower stage of the quenching tower at 160 L/hr. Throughout operation the pressure in the quenching tower was maintained at 0.05 MPaG, which was the same as that of the fluidized bed reactor, and there were no blockages. At this point, monoethanolamine was detected in the product gas by reaction running out from the top of the quenching tower. Further, the concentration of 4-methyl-4-formyl-1-cyclohexene and methacrolein in the withdrawn liquid from the upper and middle sections of the quenching tower was 1,288 ppm by weight, the concentration of benzoic acid in the withdrawn liquid from the lower section was 2,820 ppm by weight, and butadiene having a purity of 99.3% was obtained. The molecular weight of the polybutadiene obtained by polymerizing this butadiene in the same manner as in Example 1 was Mw of 215,000, Mn of 201,000, and Mw/Mn of 1.07.

Example 12

Butadiene production, quenching of the product gas by reaction, and butadiene purification were carried out in the same manner as in Example 1, except that as the quenching agent of the product gas by reaction in the step (c), an aqueous solution of 25% by weight monoethanolamine was sprayed from an upper stage and a middle stage of the quenching tower at 100 L/hr and 170 L/hr, respectively, and o-xylene was sprayed from a lower stage of the quenching tower at 160 L/hr. Throughout operation the pressure in the quenching tower was maintained at 0.05 MPaG, which was the same as that of the fluidized bed reactor, and there were no blockages. At this point, the concentration of 4-methyl-4-formyl-1-cyclohexene and methacrolein in the withdrawn liquid from the upper and middle sections of the quenching tower was 1,355 ppm by weight, the concentration of benzoic acid in the withdrawn liquid from the lower section was 2,803 ppm by weight, and butadiene having a purity of 99.2% was obtained. The molecular weight of the polybutadiene obtained by polymerizing this butadiene in the same manner as in Example 1 was Mw of 210,000, Mn of 194,000, and Mw/Mn of 1.08.

Example 13

Butadiene production, quenching of the product gas by reaction, and butadiene purification were carried out in the same manner as in Example 1, except that as the quenching agent of the product gas by reaction in the step (c), an aqueous solution of 25% by weight monoethanolamine was sprayed from an upper stage of the quenching tower at 100 L/hr, and m-xylene was sprayed from a middle stage and a lower stage of the quenching tower at 170 L/hr and 160 L/hr, respectively. Throughout operation the pressure in the quenching tower was maintained at 0.05 MPaG, which was the same as that of the fluidized bed reactor, and there were no blockages. At this point, the concentration of 4-methyl-4-formyl-1-cyclohexene and methacrolein in the withdrawn liquid from the upper section of the quenching tower was 2,702 ppm by weight, the concentration of benzoic acid in the withdrawn liquid from the middle and lower sections was 1,366 ppm by weight, and butadiene having a purity of 99.5% was obtained. The molecular weight of the polybutadiene obtained by polymerizing this butadiene in the same manner as in Example 1 was Mw of 215,000, Mn of 209,000, and Mw/Mn of 1.07.

Example 14

Butadiene production, quenching of the product gas by reaction, and butadiene purification were carried out in the same manner as in Example 1, except that as the quenching agent of the product gas by reaction in the step (c), an aqueous solution of 25% by weight monoethanolamine was sprayed from an upper stage of the quenching tower at 100 L/hr, and o-xylene was sprayed from a middle stage and a lower stage of the quenching tower at 170 L/hr and 160 L/hr, respectively. Throughout operation the pressure in the quenching tower was maintained at 0.05 MPaG, which was the same as that of the fluidized bed reactor, and there were no blockages. At this point, the concentration of 4-methyl-4-formyl-1-cyclohexene and methacrolein in the withdrawn liquid from the upper section of the quenching tower was 2,688 ppm by weight, the concentration of benzoic acid in the withdrawn liquid from the middle and lower sections was 1,374 ppm by weight, and butadiene having a purity of 99.5% was obtained. The molecular weight of the polybutadiene obtained by polymerizing this butadiene in the same manner as in Example 1 was Mw of 213,000, Mn of 199,000, and Mw/Mn of 1.07.

Comparative Example 4

Butadiene production, quenching of the product gas by reaction, and butadiene purification were carried out in the same manner as in Example 1, except that as the quenching agent of the product gas by reaction in the step (c), water was sprayed from an upper stage and a middle stage of the quenching tower at 100 L/hr and 170 L/hr, respectively, and m-xylene was sprayed from a lower stage of the quenching tower at 160 L/hr. During operation the pressure in the quenching tower increased over time. When the pressure reached 0.09 MPaG, an open inspection was carried out, whereby blockages were found in the top of the quenching tower. At this point, the concentration of 4-methyl-4-formyl-1-cyclohexene and methacrolein in the withdrawn liquid from the upper and middle sections of the quenching tower was 244 ppm by weight, the concentration of benzoic acid in the withdrawn liquid from the lower section was 2,779 ppm by weight, and butadiene having a purity of 99.0% was obtained. The molecular weight of the polybutadiene obtained by polymerizing this butadiene in the same manner as in Example 1 was Mw of 200,000, Mn of 143,000, and Mw/Mn of 1.4.

The present application is based on a Japanese patent application filed on May 19, 2011 (Japanese Patent Application No. 2011-112284), whose contents are incorporated herein by reference.

INDUSTRIAL APPLICABILITY

When producing a conjugated diolefin corresponding to a monoolefin by catalytic oxidative dehydrogenation of a hydrocarbon containing a monoolefin having 4 or more carbon atoms and molecular oxygen using a catalyst which comprises a metal oxide and a carrier, in the production method according to the present invention, a conjugated diolefin that can be preferably used as a raw material for synthetic rubber, resin and the like, can be produced by sufficiently reducing impurities that inhibit polymerization of the conjugated diolefin in a quenching step.

DESCRIPTION OF SYMBOLS

1 Reactor
2 Quenching Tower
3 Absorption Tower
4 Stabilizer
5 Flash Tower
6 Condenser
7 Extractive Distillation Column
8 Stripping Tower
9 Extractive Distillation Column
10 Distillation Column
11 Distillation Column
12 Butadiene
13 Dewatering Tower
14 Solvent Absorption Tower
15 Degassing Tower
16 Solvent Separation Tower
21 Chimney
21A Chimney
21B Chimney
21C Chimney
22 Packed Bed
22A Packed Bed
22B Packed Bed
22C Packed Bed
23A Spray Apparatus
23B Spray Apparatus
23C Spray Apparatus
23D Spray Apparatus
24A Pump
24B Pump
24C Pump
24D Pump
25A Decanter
25B Decanter
25C Decanter
25D Decanter
31 Product Gas by Reaction
32 Product Gas by Reaction after Quenching (Washing)
33 Flow of Gas
41 Quenching Agent

What is claimed is:

1. A method for producing a conjugated diolefin, comprising:
a step of feeding a hydrocarbon containing a monoolefin having 4 or more carbon atoms and oxygen to a reactor accommodated with a catalyst which comprises a metal oxide and a carrier to produce a product gas by reaction containing a conjugated diolefin; and
a step of sending the product gas by reaction to a quenching tower and washing the gas with a quenching agent, wherein an organic amine aqueous solution is used as the quenching agent.

2. The method for producing the conjugated diolefin according to claim 1, wherein an aromatic organic solvent is used in combination as the quenching agent.

3. The method for producing the conjugated diolefin according to claim 1 or 2, wherein a withdrawn liquid from the quenching tower contains at least one compound selected from the group consisting of 4-methyl-4-formyl-1-cyclohexene, methacrolein, methacrylic acid, benzoic acid, acetic acid, acrylic acid, and an organic amine salt thereof.

4. The method for producing the conjugated diolefin according to claim 1 or 2, wherein the quenching tower has a plurality of vertical sections, an aromatic organic solvent is used as the quenching agent at a lowest section among the plurality of sections, and an organic amine aqueous solution is used as the quenching agent at a section above the lowest section.

5. The method for producing the conjugated diolefin according to claim 1 or 2, wherein the organic amine contains at least one compound selected from the group consisting of monoethanolamine, diethanolamine, and triethanolamine.

6. The method for producing the conjugated diolefin according to claim 2, wherein the aromatic organic solvent contains at least one compound selected from the group consisting of o-xylene, m-xylene, p-xylene, and a mixed xylene.

7. The method for producing the conjugated diolefin according to claim 1 or 2, wherein the metal oxide is represented by the following experimental formula (1):

$$Mo_{12}Bi_pFe_qA_aB_bC_cD_dE_eO_x \quad (1)$$

wherein A represents at least one element selected from the group consisting of nickel and cobalt; B represents at least one element selected from the group consisting of alkali metal elements; C represents at least one element selected from the group consisting of magnesium, calcium, strontium, barium, zinc, and manganese; D represents at least one element selected from the group consisting of rare earth elements; E represents at least one element selected from the group consisting of chromium, indium, and gallium; O represents oxygen; p, q, a, b, c, d, e, and x denote an atomic ratio of bismuth, iron, A, B, C, D, E, and O, respectively, to 12 molybdenum atoms, where $0.1 \leq p \leq 5$, $0.5 \leq q \leq 8$, $0 \leq a \leq 10$, $0.02 \leq b \leq 2$, $0 \leq c \leq 5$, $0 \leq d \leq 5$, and $0 \leq e \leq 5$; and x denotes the number of oxygen atoms required to satisfy valence requirements of other elements that are present.

8. The method for producing the conjugated diolefin according to claim 1 or 2, wherein the reactor is a fluidized bed reactor.

* * * * *